US012653510B2

(12) United States Patent
    Albert

(10) Patent No.: US 12,653,510 B2
(45) Date of Patent: Jun. 16, 2026

(54) DEVICE FOR POSITIONING AN ABSORPTIVE MATRIX ELEMENT WITHIN A BODY CAVITY AND KIT FOR COLLECTING BIOLOGICAL SECRETIONS

(71) Applicant: Noselab GmbH, Munich (DE)

(72) Inventor: Mareike Albert, Munich (DE)

(73) Assignee: Noselab GmbH, Munich (DE)

( * ) Notice: Subject to any disclaimer, the term of this patent is extended or adjusted under 35 U.S.C. 154(b) by 1240 days.

(21) Appl. No.: 17/523,908

(22) Filed: Nov. 11, 2021

(65) Prior Publication Data

US 2022/0142618 A1      May 12, 2022

(30) Foreign Application Priority Data

Nov. 11, 2020    (EP) ..................................... 20206895

(51) Int. Cl.
    *A61B 10/00*          (2006.01)
    *A61F 13/20*          (2006.01)
                          (Continued)

(52) U.S. Cl.
    CPC ...... *A61B 10/0045* (2013.01); *A61F 13/2005* (2013.01); *A61F 13/266* (2013.01); *A61F 13/34* (2013.01)

(58) Field of Classification Search
    CPC ............... A61B 10/0045; A61B 10/02; A61B 2010/0216; A61F 13/2005; A61F 13/266; A61F 13/34; A61F 2013/8473
    See application file for complete search history.

(56) References Cited

U.S. PATENT DOCUMENTS

| | | | |
|---|---|---|---|
| 2,879,769 A | 3/1959 | Gordon et al. | ................ 128/263 |
| 3,815,580 A | 6/1974 | Oster | ..................... A61B 10/00 |
| | | | 128/2 W |

(Continued)

FOREIGN PATENT DOCUMENTS

| | | |
|---|---|---|
| CA | 2371883 A1 | 6/2000 |
| GB | 2153684 A | 1/1985 |

(Continued)

OTHER PUBLICATIONS

Extended European search report dated Dec. 11, 2024, from the European Patent Office in the parent European application EP24190310.3 (10 pages).

(Continued)

*Primary Examiner* — Rebecca E Eisenberg
*Assistant Examiner* — Gabriella E Burnette
(74) *Attorney, Agent, or Firm* — Imperium Patent Works; Darien K. Wallace

(57)        ABSTRACT

An application device for positioning an absorptive matrix (AM) element within a body cavity includes a tube, the AM element, a release element and a deflector. The AM element is disposed inside the tube in a stored state before exiting the tube towards the distal end in a released state. The release element slides inside the tube along a longitudinal axis of the tube and pushes the AM element out of the tube towards the distal end of the tube as the release element slides farther into the tube. The deflector is disposed at the distal end of the tube and bends the AM element away from the longitudinal axis of the tube as the AM element is pushed out of the tube. The deflector is an extension of the wall of the tube that protrudes from the distal end and bends inward towards the longitudinal axis of the tube.

21 Claims, 9 Drawing Sheets

(51) Int. Cl.
    *A61F 13/26*       (2006.01)
    *A61F 13/34*       (2006.01)

(56)         References Cited

U.S. PATENT DOCUMENTS

| | | | |
|---|---|---|---|
| 4,895,559 A | 1/1990 | Shippert | A61F 13/20 604/15 |
| 5,267,953 A | 12/1993 | Paul et al. | A61F 13/20 604/15 |
| 5,507,807 A * | 4/1996 | Shippert | A61M 31/00 604/59 |
| 6,186,973 B1 | 2/2001 | Buzot | A61F 13/20 604/17 |
| 6,517,509 B1 | 2/2003 | Shippert | A61F 13/20 604/11 |
| 6,786,883 B2 * | 9/2004 | Shippert | A61F 13/26 604/385.18 |
| 7,320,673 B2 * | 1/2008 | Gann | A61F 13/26 604/385.18 |
| 11,779,431 B2 * | 10/2023 | Ranpura | A61B 90/39 600/432 |
| 2003/0157728 A1 * | 8/2003 | Uhl | A61B 10/0096 422/946 |
| 2006/0283464 A1 * | 12/2006 | Dunlap | A61M 16/0461 128/206.28 |
| 2007/0014830 A1 * | 1/2007 | Tijsma | A61K 31/65 424/426 |
| 2009/0187098 A1 | 7/2009 | Makower et al. | A61B 6/12 600/424 |
| 2009/0216150 A1 | 8/2009 | Reichel et al. | A61B 10/00 600/562 |

FOREIGN PATENT DOCUMENTS

| | | | |
|---|---|---|---|
| JP | | 2011-169855 A | 2/2011 |
| WO | WO 2012/168520 | | 5/2012 |

OTHER PUBLICATIONS

Extended European search report dated Apr. 30, 2021, from the European Patent Office in the parent European application EP20206895.3 (7 pages).

Office action of the Japanese Patent Office in a related Japanese patent application JP 2023-550716 dated Sep. 2, 2025, as well as the English translation of the Japanese Office action (6 pages).

* cited by examiner

DETAILED AREA X FROM FIG. 2A

DETAILED AREA Y FROM FIG. 3A

L_s LONGITUDINAL AXIS OF AM ELEMENT

11 DISTAL END

15 SPINE ELEMENT

10 AM ELEMENT

12 PROXIMAL END

13 LEASH

CAP
304

OUTER
VESSEL
301

AM
ELEMENT
10

INNER
VESSEL
302

300
VESSEL
ARRANGEMENT

303

305
COLLECTION
OF
SECRETION

DEVICE FOR POSITIONING AN ABSORPTIVE MATRIX ELEMENT WITHIN A BODY CAVITY AND KIT FOR COLLECTING BIOLOGICAL SECRETIONS

CROSS REFERENCE TO RELATED APPLICATION

This application is based on and hereby claims the benefit under 35 U.S.C. § 119 from European Patent Application No. EP 20206895.3, filed on Nov. 11, 2020, in the European Patent Office. This application is a continuation-in-part of European Patent Application No. EP 20206895.3, the contents of which are incorporated herein by reference.

TECHNICAL FIELD

The present invention relates to an application device for positioning an absorptive matrix (AM) element within a cavity of a human or animal body and to a collection kit that includes the application device. The present invention further relates to a method of using the application device or the collection kit for collecting nasal secretion.

BACKGROUND

Nasal secretions from the nasal cavity includes a number of proteins. These proteins are, for example, biological markers of inflammatory processes. Accordingly, the analysis of nasal secretions is a field of scientific and medical interest. For investigating inflammatory processes and allergies, the analysis is generally performed on secretions collected from the lower portion and the middle portion of the nasal cavity.

For collecting nasal secretion, different sampling techniques such as nose-blowing, suction, nasal lavage and nasosorption are used. For nasosorption, an absorptive material such as a sponge, a cotton swab or a synthetic absorptive matrix (SAM) element is placed within the nasal cavity for a short period of time, for example, for one minute. For collecting nasal secretion from the upper portion of the nasal cavity, more specifically from the olfactory cleft, positioning the absorptive material is generally challenging because the olfactory cleft is located in the upper part of the nose, which is difficult to reach and dangerously close to the base of the skull.

Various known sampling techniques result in a considerable variability in the amount of proteins captured. For example, nasal lavage leads to an uncontrollable dilution of the secretion and to a possible loss of markers via the mouth/nasopharynx. This hinders further research in the field because data from different studies using different sampling techniques cannot be compared. Even the same sampling technique may cause variability in the nasal secretion collected. In the case of nasosorption, for example, variability may result from the difficulty of correctly and reproducibly positioning the absorptive material at an intended, predetermined target position, for example, in the olfactory cleft and/or from contamination of the absorptive material caused by injury or irritation of the nasal mucosa during the insertion of the material into the nose.

Despite the known problems associated with collecting nasal secretions, there is no standardized procedure for collecting such secretions, in particular for collecting nasal secretions from the upper portion of the nasal cavity. Likewise, there is no tool for collecting nasal secretions in a standardized manner.

Therefore, new tools for collecting nasal secretions are needed.

SUMMARY

In a first aspect, the present invention relates to an application device for positioning an absorptive matrix (AM) element within a cavity of a human or animal body, the application device comprising:
- a storage and release tube having a distal end and a proximal end, the tube being configured to store and release an AM element;
- the AM element being stored within an inner space of the tube;
- a release element being slidably supported with respect to the tube along a longitudinal axis of the tube, the release element being configured to release the AM element from the tube;
- at least one deflection means arranged at the distal end of the tube, the deflection means being capable of bending the AM element away from the longitudinal axis of the tube when the AM element is released from the tube, wherein the AM element is not fixedly attached to any of the tube, the release element or the deflection means.

In a second aspect, the present invention relates to a collection kit for collecting biological secretions from a cavity of a human or animal body comprising the application device of the invention, wherein the collection kit further comprises a vessel arrangement for storing the AM element after the collection of the secretions.

In a third aspect, the present invention relates to a method of using the application device or the collection kit for collecting nasal secretions.

An application device for positioning an absorptive matrix (AM) element within a body cavity includes a tube, the AM element, a release element and a deflector. The tube has a wall, a distal end and a proximal end. The AM element is disposed inside the tube in a stored state before exiting the tube towards the distal end of the tube in a released state. The release element slides inside the tube along a longitudinal axis of the tube and pushes the AM element out of the tube towards the distal end of the tube as the release element slides farther into the tube. The deflector is disposed towards the distal end of the tube and bends the AM element away from the longitudinal axis of the tube as the AM element is pushed out of the tube. In one embodiment, the release opening is at the distal end of the tube, and the deflector is an extension of the wall of the tube that protrudes from the distal end and bends inward towards the longitudinal axis of the tube. In another embodiment, the release opening is located in the wall of the tube towards the distal end, and the deflector is formed by a thickened part of a wall portion near the distal end.

A method for collecting nasal secretions involves releasing an AM element into the nasal cavity of a person. A distal end of a tube of an application device is introduced into the nasal cavity. The tube has a wall, the distal end and a proximal end. The AM element is disposed inside the tube in a stored state before exiting the tube in a released state. A deflector is disposed towards the distal end of the tube. The AM element is released into the nasal cavity by sliding a release element into the tube such that the release element pushes the AM element out of the tube towards the distal end. The deflector bends the AM element away from the longitudinal axis of the tube as the AM element is pushed out of the tube. In one example, the deflector is a portion of the wall of the tube that protrudes from the distal end and bends inward towards the longitudinal axis of the tube. As the release element slides farther into the tube, the release element pushes the AM element out of the distal end of the tube. The AM element is then deflected by the deflector away from the longitudinal axis of the tube. In another example, the deflector is a thickened part of a wall portion of the tube near the distal end. As the release element slides farther into the tube, the release element pushes the AM element out of the release opening located in the wall of the tube towards the distal end. The AM element is deflected by the deflector formed by the thickened wall portion and then is pushed out of the release opening in a direction away from the longitudinal axis of the tube. The tube is removed from the nasal cavity without removing the AM element from the nasal cavity. Then the AM element is removed from the nasal cavity, for example, after the elapse of at least fifteen minutes.

Other embodiments and advantages are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

DETAILED DESCRIPTION

Reference will now be made in detail to some embodiments of the invention, examples of which are illustrated in the accompanying drawings.

Figure 2A:
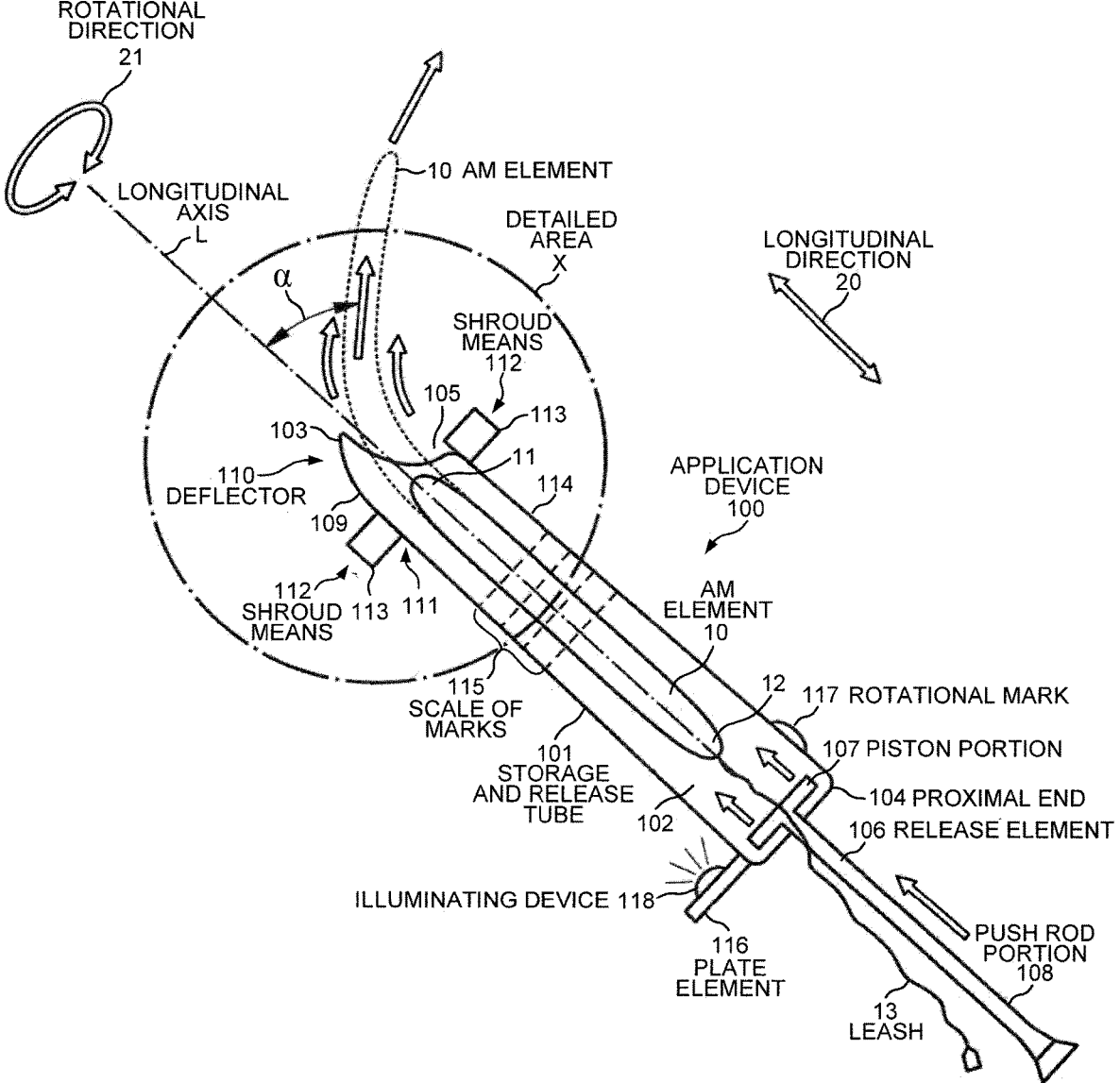
FIG. 2A shows a perspective view of a first embodiment of an application device according to the invention with an AM element in its storage (retracted) position and an AM element in its partially released position.

FIG. 2A shows a first aspect of the present invention involving an application device 100 for positioning an absorptive matrix (AM) element 10 within a cavity of a human or animal body, such as a nasal cavity. The application device 100 comprises:

a storage and release tube 101 having a distal end 103 and a proximal end 104, the tube being configured to store and release the AM element 10;

the AM element 10 being stored within an inner space of the tube 101;

a release element 106 being slidably supported with respect to the tube 101 along a longitudinal axis of the tube, the release element being configured to release the AM element 10 from the tube; and at least one deflection means 110 arranged at the distal end 103 of the tube 101, the deflection means being capable of bending the AM element 10 away from the longitudinal axis of the tube 101 when the AM element 10 is released from the tube. The AM element 10 is not fixedly attached to any of the tube 101, the release element 106 or the deflection means 110.

The application device 100 is applicable for positioning the AM element 10 within the cavity of the human or animal body. The AM element 10 is to be positioned within the cavity, for example, for collecting biological secretions from the cavity in a non-invasive manner. The secretions are collected by absorption of the secretions by the AM element 10. Accordingly, the application device 100 can also be referred to as a collecting device or a collection device. The collection process can also be referred to as an extraction process.

The absorptive matrix, also referred to as absorptive material, of the AM element 10 can be a synthetic absorptive matrix, a non-synthetic absorptive matrix, or a mixture of synthetic and non-synthetic absorptive matrices.

In case of a synthetic absorptive matrix, the AM element 10 is also referred to as a synthetic absorptive matrix (SAM) element.

In case of a non-synthetic (i.e., natural) absorptive matrix, the matrix preferably is a cotton matrix or a cellulose matrix.

The cavity is typically a nasal cavity. The application device 100 is particularly suitable for positioning the AM element 10 in the upper portion of the nasal cavity, more specifically in the olfactory cleft, and thus for collecting nasal secretions from this region. The olfactory cleft is a narrow passage located in the upper part of each of the left nasal cavity and the right nasal cavity. The olfactory cleft has a special type of covering, namely the olfactory epithelium, that is different from other regions of the nasal cavity. Accordingly, with few exceptions, a different type of mucous membrane surface is found in the remaining portion of the nasal cavity. The septum, the medium turbinates and the lower turbinates of the nasal cavity are not covered by the olfactory epithelium.

Accordingly, one of the most relevant applications of the application device 100 is to position the AM element 10 in the upper portion of the nasal cavity for collecting nasal secretions from this region. The nasal secretions collected from this region includes nasal secretions located on and in the upper layers of the olfactory epithelium. The dimensions of the AM element 10 are selected in a manner that facilitates collecting the nasal secretion along the entire sagittal extension and the entire width of the olfactory cleft. The analysis of nasal secretions is a field of growing scientific and medical interest. For example, for some diseases, the analysis of nasal secretions may be used as a non-invasive diagnostic approach that is broadly available.

Nasal secretions are preferably collected from the olfactory cleft of each of the left nasal cavity and the right nasal cavity of a subject. To do so, one application device per cavity is applied. The collection may be performed at the same time. After collection, the secretion of the left nasal cavity and the secretion of the right nasal cavity may be combined for further analysis.

In another example, the cavity is an oral cavity. The application device 100 is suitable for positioning the AM element 10, for example, between the buccal mucosa of the cheek and the teeth in the upper or lower alveolar ridge for collecting secretion from this region. In this case, the biological secretion that is collected is saliva. After collection, the saliva may be analyzed, for example, for the presence of human papilloma virus (HPV). HPV-associated tumors of the oral cavity, such as oral cavity squamous cell carcinoma, are a common form of cancer. The saliva may also or alternatively be analyzed for Herpes simplex virus-associated proteins.

In yet another example, the cavity is an auditory canal. In this case, the biological secretion that is collected is ceruminal liquid.

The storage and release tube 101 has a distal end 103 and a proximal end 104. The term "distal end" as used herein refers to the end that points away from the operator of the device and towards the cavity in which the device is to be inserted. Accordingly, the AM element 10 is to be released from the tube 101 at the distal end 103 or at a distal end portion of the tube. The term "proximal end" as used herein refers to the opposite end of the tube 101, i.e., the end that points towards the operator of the device and away from the cavity in which the device is to be inserted. The proximal end 104 of the tube 101 is thus closer to the operator of the device than the distal end 103 of the tube.

The tube 101 is configured to store and release the AM element 10. The AM element is stored within an inner space of the tube 101. The AM element 10 is to be released from the tube 101 after insertion of the tube into the cavity. The AM element 10 is to be released from the distal end or from a distal end portion of the tube 101. The release of the AM element 10 is mediated by the release element 106. The release element 106 is slidably supported with respect to the tube 101 along a longitudinal axis of the tube. By releasing the AM element 10 from the tube 101, the AM element is deposited at a predetermined, target position within the cavity.

The AM element 10 is intended to be stored in the tube 101 in an essentially linear form, i.e., in an essentially straight manner with preferably no angles. The AM element 10 is intended to be bent only once, namely when the AM element is released from the tube 101. This will be further described in connection with the description of the deflection means 110 below.

The AM element 10 need not necessarily extend along the entire longitudinal extension of the inner space of the tube 101. The tube 101 may have a longitudinal length that is considerably longer than the longitudinal length of the AM element 10. In this case, the AM element 10 is preferably stored towards the distal end 103 or in the distal end portion of the tube 101 because the AM element 10 is to be released from the distal end or from the distal end portion of the tube.

The tube 101 may be essentially straight or the tube may have a slight curvature in a proximal end portion of the tube. In case the tube 101 has the curvature, and the AM element 10 is intended to be positioned in the upper portion of the nasal cavity for collecting nasal secretions located in the olfactory cleft, the curvature of the tube 101 is configured to point towards the septum (i.e., medial) during the insertion of the tube into the nasal cavity. In other words, the proximal end portion of the tube 101 is bent towards the septum. Such a curvature facilitates the correct positioning of the tube 101, in particular by facilitating the correct insertion route of the tube along the septum towards the upper portion of the nasal cavity. Specifically, the curvature avoids deviating from the correct insertion route in a lateral direction. In case the tube 101 has the curvature in the proximal end portion of the tube, an angle β, between the septum and the proximal end 104 of the tube preferably is smaller than or equal to 45°, more preferred smaller than or equal to 30°, further preferred between 5° and 30°, further preferred around 20°. It is preferred that the curvature in the proximal end portion of the tube 101 does not cause the AM element 10 stored within the tube to be bent within the tube 101. This can be achieved, for example, by storing the AM element 10 in the distal end portion of the tube 101.

The application device 100 allows positioning the AM element 10 within the cavity in a targeted and standardized manner, which in turn allows collecting the secretions in a standardized manner. This significantly decreases variability in the type and amount of secretions that are absorbed by the AM element 10 when compared to other means of positioning the AM element, such as a positioning by hand.

The design of the application device 100 allows positioning the AM element 10 within the cavity in a targeted, easy and reliable manner. In line with this, the design of the application device 100 minimizes the risk of injury to the patient during the positioning of the AM element 10, thereby increasing the comfort of the patient and reducing variations in the collected secretions that are caused by injury or irritation (such as traces of tissue or blood). This is particularly relevant in case the AM element 10 is to be positioned in the olfactory cleft, i.e., in general above the lower and the middle nasal turbinates, lateral to the upper nasal turbinates and below the olfactory fibers because this region is very sensitive. In some patients, the anatomy of the nasal cavity is such that the olfactory cleft is located lateral to the middle nasal turbinates rather than lateral to the upper nasal turbinates.

The effect of reliably positioning the AM element 10 while minimizing the risk of injury is primarily achieved by causing the AM element to be bent and/or deflected upon release of the AM element from the tube 101. The deflector 110 is capable of bending the AM element 10 away from the longitudinal axis of the tube 101 when the AM element is released from the tube. The AM element 10 thus acquires a curvature during its release from the tube 101. The deflection means 110 is capable of bending the AM element 10 away from the longitudinal axis of the tube 101 in a predefined direction. This ensures that the AM element 10 is positioned at its predetermined target position within the cavity. By causing the AM element 10 to be bent and/or deflected upon release of the AM element from the tube 101, contact and contact forces between the AM element and a mucosa (or other anatomical boundary) that lines the cavity are minimized. This increases the safety and comfort of the patient.

Each element that causes the AM element 10 to be bent and/or deflected upon release of the AM element from the tube 101 can be regarded as a deflector, a deflection means or a means for deflection 110. The bending or deflection leads to a release direction of the AM element 10 that is inclined with respect to the longitudinal axis of the tube 101 by a deflection angle α that is greater than 0°.

In case the AM element 10 is to be positioned in the upper portion of the nasal cavity for collecting nasal secretions located in the olfactory cleft, the deflector or deflection means 110 causes the AM element to bend in a caudal and sagittal anatomical direction.

The deflector or deflection means 110 renders the application device 100 suitable for positioning the AM element 10 in the upper portion of the nasal cavity for collecting nasal secretion located in the olfactory cleft. To reach this region of the nasal cavity, an AM element 10 that is not caused to be bent during its release, i.e., that is released in a straight or linear form in line with the longitudinal axis of the tube 101 would not be suitable. Due to the anatomy of the nasal cavity, a straight form upon release may be suitable for reaching the lower portion or the middle portion of the nasal cavity, but not for reaching the upper portion in which the olfactory cleft is located.

Depending on the degree of deflection of the AM element 10 upon release of the AM element, the application device 100 may also be used for positioning the AM element in the lower portion or the middle portion of the nasal cavity.

The release direction of the AM element 10 is inclined with respect to the longitudinal axis of the tube 101 by the angle α, which is greater than 0°. The angle α is predefined by the design of the application device 100, in particular by the design of the deflector 110.

For positioning the AM element 10 in the upper portion of the nasal cavity, the angle α is preferably greater than 0° and smaller than or equal to 50°, preferably between 20° and 45°.

For positioning the AM element 10 in the middle portion of the nasal cavity, the angle α preferably is greater than 0° and smaller than or equal to 30°, preferably between 5° and 15°.

For positioning the AM element 10 in the lower portion of the nasal cavity, the angle α preferably is greater than 0° and smaller than or equal to 20°.

Depending on the individual anatomy of the nasal cavity of a given patient, the operator of the application device 100 may adapt the positioning of the tube 101 to ensure that the AM element 10 reaches its intended, predetermined target position upon its release from the tube 101. For example, the operator may choose a steeper degree of insertion of the tube 101 into the cavity.

For easily adapting the positioning of the tube 101 according to the individual anatomy of the patient, the distal end portion of the tube can preferably be easily bent by the operator.

Due to the deflector 110, the distal end 103 or the distal end portion of the tube 101 does not need to be positioned such that it directly points to the intended, predetermined target position of the AM element 10. It is rather possible to halt the insertion of the tube 101 before directly pointing to the target position at a location and a distance that is suitable for positioning the AM element at the target position upon its release from the tube 101.

Figure 3A:
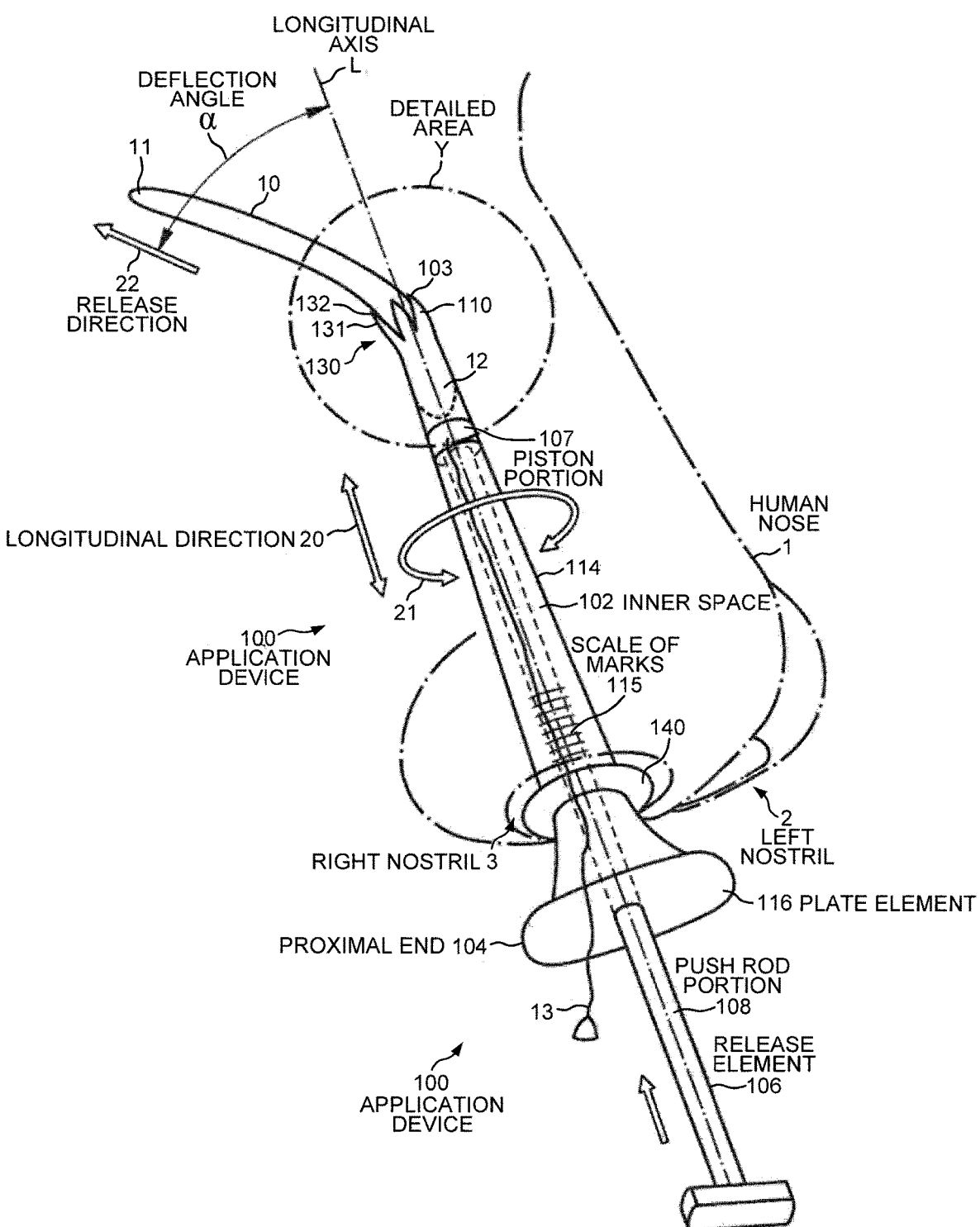
FIG. 3A shows a perspective view of a second embodiment of an application device according to the invention with an AM element in its partially released position.

Regarding the safety of the patient, in addition to the deflector 110, the risk of injury is preferably further reduced by at least one stoppage land 140 protruding from the outer circumferential surface of the tube 101. FIG. 3A shows the stoppage land 140, which limits the insertion depth of the tube 101 in the cavity. Another preferred measure for minimizing the risk of injury is to choose a material of the tube 101 in such a manner that the deformability of the tube at its distal end 103 is higher when compared to the deformability at its proximal end 104. The distal end 103 of the tube 101 is preferably made of a soft material that is bendable in a rubberlike manner. These optional measures are particularly useful for minimizing the risk of injury of the base of the skull in case the AM element 10 is to be positioned in the olfactory cleft.

A further advantage of the application device 100 is that the secretion that is absorbed by the AM element 10 after its release from the tube 101 is exclusively absorbed from the intended target position of the AM element 10 and is thus very pure. The AM element 10 is protected from any unintended contacts within the cavity by being stored in the tube 101 during its insertion into the cavity and along the entire route for reaching the location that is suitable for positioning the AM element 10 at the intended, predetermined target position, for example, in the upper part of the nasal cavity. Therefore, there is no risk of contamination of the absorptive matrix of the AM element 10 by secretions or fluids absorbed during insertion of the AM element 10 into the cavity. Likewise, there is no risk of dilution of the secretions or of bacterial or dust contamination of the secretions by fluid absorbed during insertion of the AM element 10 into the cavity, in particular in case the tube 101 is inserted into the nasal cavity through the respective nostril. For example, in case the AM element 10 is to be positioned in the olfactory cleft by hand rather than by using the application device 100, contamination and dilution of the target secretion can easily occur if the AM element 10 wipes along the mucosa in the lower parts of the nasal cavity during its insertion into the nose. Such types of contamination and dilution are a major source of variability in the type and amount of secretion that is absorbed by the AM element 10. The extent of such types of contamination and dilution also depends on the experience of the operator who collects the secretion. Using the application device 100 for positioning the AM element 10 at its intended target position avoids undesired contamination and dilution of the secretions collected by the AM element 10. This results in a much better quality of the secretions collected. It also results in a higher reproducibility of secretion collection. This contributes to collecting the secretions in a standardized manner.

Avoiding undesired contamination and dilution of the secretions collected by the AM element 10 also increases the sensitivity of the subsequent analysis of the secretions.

By having the AM element 10 protected from any unintended contacts within the cavity by being stored in the tube 101 during its insertion into the cavity, there is also no risk of incomplete absorption of secretion at the intended target position. Such incomplete absorption could be caused by a reduction of the absorptive capacity of the AM element 10 at the target position due to fluid absorbed during insertion of the AM element into the cavity.

During the removal of the AM element 10 from the cavity after the collection of secretion, undesired contamination and dilution of the secretion collected by the AM element is less likely because the absorptive capacity of the AM element is strongly reduced at this time.

In a preferred embodiment, the dimensions of the AM element 10 are selected in a manner such that the absorptive capacity of the AM element is close to zero after collecting the intended secretion for an intended collection time. This further avoids undesired contamination and dilution of the secretion collected by the AM element during the removal of the AM element from the cavity.

Due to the usage of the application device 100 for positioning the AM element 10 at its intended target position, the collected secretion is very pure, non-diluted and well defined. This cannot be achieved by known sampling techniques.

The AM element 10 is not fixedly attached to any of the tube 101, the release element 106 or the deflector 110. In other words, the AM element 10 is not fixedly attached to any other part of the application device 100. This allows leaving the AM element within the cavity, in particular within the nasal cavity, without the need to leave the storage and release tube 101 within the cavity at the same time. Accordingly, after the release of the AM element 10 from the tube 101, the tube can be removed from the cavity while the AM element remains in the cavity.

In one embodiment, the tube 101 can then be refilled with a second AM element 10 for further use, for example, for positioning the second AM element 10 in a second nostril of the patient after having positioned a first AM element 10 in a first nostril of the patient by using the application device 100.

However, in a preferred embodiment, the application device 100 is a single-use device. For practical and hygienic reasons, it is preferable for the application device 100 to be a single-use product. Accordingly, a first application device 100 is used for positioning a first AM element 10 in a first nasal cavity through a first nostril of the patient, and a second application device 100 is used for positioning a second AM element 10 in a second nasal cavity through a second nostril of the patient. After collection, the secretion of the first nasal cavity and the secretion of the second nasal cavity may be combined for further analysis.

The removal of the tube 101 from the cavity after the AM element 10 is released and thereby deposited at its predetermined target position allows the AM element 10 to be left in the cavity for a relatively long period of time, for example for fifteen minutes, without discomfort to the patient caused by the tube 101. It thus allows longer collection times compared to a situation in which the tube 101 also needs to remain within the cavity. This is an important advantage of the application device 100, in particular in case the AM element 10 is used for collecting nasal secretion from the olfactory cleft. Given that the amount of nasal secretion is very low, a long collection time, which corresponds to a long residence time of the AM element 10 within the cavity, such as, for example, fifteen minutes, may be needed in order to collect a sufficient amount of nasal secretion for subsequent analysis. Such long collection times can only be achieved by removing the tube 101 from the nasal cavity while the AM element 10 remains in the cavity. Having the tube 101 in the nose would present a constant danger of the tube causing damage to the skull base and/or bleeding of the nasal mucosa. Further, the tube 101 would cause a permanent irritation of the nose because the nasal cavity is narrow and very sensitive, especially in the region of the olfactory cleft. It would thus not be comfortable for the patient to have the tube 101 in the nose during the entire time of secretion collection. In addition, due to the permanent irritation caused by the tube 101, the patient would not be able to sit still for the required collection time without anesthesia.

Extended collection times such as, for example, fifteen minutes, cannot be achieved by known sampling techniques, in particular in case nasal secretion from the upper portion of the nasal cavity is to be collected.

When using the application device 100, there is no limit on the amount of time during which the AM element 10 can be used to collect biological secretions.

Taken together, the application device 100 has improved characteristics in at least three aspects. The first aspect concerns the positioning of the AM element 10 and thus the location of the AM element in the cavity. The application device 100 allows positioning the AM element within the cavity in a targeted and standardized manner, which in turn allows secretions to be collected in a standardized manner. The application device 100 is particularly suitable for positioning the AM element 10 in the upper portion of the nasal cavity, more specifically in the olfactory cleft. The second aspect concerns the purity of the secretion that is collected. The collected secretion is very pure, non-diluted and well defined. The third aspect concerns the time of secretion collection. There is no time limit for the collection period.

In a preferred embodiment, a first application device 100 for positioning a first AM element 10 in a right nasal cavity and a second application device 100 for positioning a second AM element 10 in a left nasal cavity are provided. The first and second application devices are preferably mirror images of each other. For example, the location of a rotational mark provided on the outer circumferential surface of the tube 101 or visible from the outside of the tube preferably is mirror-inverted when comparing the first and the second application devices. The rotational mark is described in more detail below. In case the tube 101 has the curvature towards the septum in the proximal end portion of the tube, the curvature may also be mirror-inverted when comparing the first and the second application devices.

The application device 100 can easily be bent and squeezed without causing contact forces that are too strong in case of contact of the device with a mucosa lining the cavity. This increases the safety and comfort of the patient. Accordingly, the storage and release tube 101 is preferably made from a flexible material that can easily be deformed. For example, the storage and release tube 101 can be made from soft plastic or soft silicone. The material is also selected to be biocompatible and to be generally suitable for medical devices.

In a preferred embodiment, at least in a pre-usage stage of the device, a release opening or exit opening of the tube 101 is closed by a closure. The release opening is preferably closed by the closure until the release process of the AM element 10. The closure additionally protects the AM element 10, in particular the distal end 11 of the AM element, from potential contamination through the release opening. The release opening may be located at the distal end 103 of the tube 101 or in a side wall of the tube at a distal end portion of the tube.

In a preferred embodiment, the closure and at least a distal end portion of the AM element 10 are configured to open the closure by pushing forward the distal end 11 of the AM element 10 when the AM element is released from tube 101. The closure protects the AM element from potential contamination until the release of the AM element from the tube 101. In particular, the closure protects the AM element 10 from potential contamination during its insertion into the cavity.

The closure may be a film attached to the release opening. The film may be attached, for example, by gluing or welding. The film, for example a thin plastic sheet, needs to stay connected to the tube 101 after the AM element 10 has been pushed through the film so that the film does not get lost within the cavity.

In a preferred embodiment, the closure is a tongue closure comprising a plurality of tongues. The plurality of tongues may form a tapered tip. The advantage of closing the release opening of the tube 101 by a tongue closure is that the tongue closure can be opened by a pushing force applied to the AM element 10 only. This is due to a bendability of the tongues of the tongue closure. No additional opening means for opening the closure are necessary.

In a preferred embodiment, the application device 100 further comprises at least one shroud means 112 located within a transition region of the tube 101 and the deflector 110. The transition region is the region in which a contact between the storage and release tube 101 and the nasal mucosa is most likely. The provision of the shroud means 112 further minimizes contact and/or contact forces between the storage and release tube 101 and the anatomical boundaries of the cavity, such as contact and/or contact forces between the tube and the nasal mucosa of the nasal cavity. The shroud means 112 also serves as a damper means to soften a possible contact between the storage and release tube 101 and the nasal mucosa. This further increases the comfort of the patients during the insertion of the device and the release of the AM element 10 and, more importantly, decreases the risk of injury of the patient. Likewise, it further increases the acceptance of the procedure by the patients.

In a preferred embodiment, the shroud means 112 comprises a cushion element 113 arranged along an outer circumferential surface of the transition region. The shroud means 112 preferably comprises a plurality of cushion elements 113 arranged along the outer circumferential surface of the transition region. By forming the shroud means 112 from a plurality of cushion elements that are arranged along the outer circumferential surface of the transition region, any possible contact between the storage and release tube 101 and the nasal mucosa can be softened.

The cushion element 113 can be formed as a ring-like element surrounding the outer circumferential surface. Alternatively, a plurality of single cushion elements are arranged along the outer circumferential surface. The cushion element(s) is/are arranged at positions of the application device 100 that may contact the anatomical boundaries of the cavity, such as the nasal mucosa of the nasal cavity. A ring-like element or a ring-like arrangement of the plurality of cushion elements is preferred because it allows using the application device 100 for both the left and the right nasal cavity.

In a preferred embodiment, the storage and release tube 101 is at least partially coated with a soft material that serves as the damper means to soften a possible contact between the storage and release tube 101 and the nasal mucosa.

In a preferred embodiment, the application device 100 further comprises a spreader device having spreading arm means 201, wherein the application device 100 is attachable to one of the spreading arm means and can thereby be arranged in a gap between the spreading arm means. The spreading arm means 201 is preferably connected with or mounted to the application device 100. The spreading arm means 201 ensures a sufficient gaping of the opening of the cavity. This facilitates the insertion of the application device 100 into the cavity. This is particularly relevant for the nasal cavity, which is often rather narrow. The spreading arm means 201 may be configured to open the nose in a vertical direction by pushing the nostril upward.

In a preferred embodiment, a scale of marks 115 is provided on the tube 101 along a longitudinal direction of the tube, the scale of marks indicating the insertion depth of the tube into the cavity of the human or animal body. The scale of marks is located within a suitable region of the storage and release tube 101. When compared with a visible boundary or edge of the cavity of interest, the scale of marks 115 provides information about the insertion depth of the application device 100 in the cavity. Thus, the operator can easily detect the insertion depth of the tube 101. In this way, the tube 101 can easily and controllably be inserted at an insertion depth suitable for positioning the AM element 10. The controlled insertion also decreases the risk of injury to the patient.

In a preferred embodiment, at least one stoppage land 140 is provided that protrudes from the outer circumferential surface of the tube 101. The stoppage land 140 is a ring land or at least one plate-like land protruding from the outer circumferential surface in the vicinity of the proximal end 104 of the tube 101. The stoppage land 140 limits the insertion depth of the tube 101 into the cavity, thereby decreasing the risk of injury to the patient.

In a preferred embodiment, the at least one stoppage land 140 is arranged proximally to the scale of marks.

In a preferred embodiment, the deflector 110 is formed by an extended wall portion of the tube 101 protruding from the distal end 103 of the tube 101 and inclined with respect to the longitudinal axis towards the longitudinal axis. The extended wall portion can also be referred to as an extended end wall portion. The extended wall portion is a simple way of forming and providing the deflector 110. It can also easily be integrated into the tube 101 during the production of the tube. The extended wall portion is preferably formed integrally with the storage and release tube so that there is no risk of loosening of the deflector 110 within the cavity.

In a preferred embodiment, a tongue closure comprising a plurality of tongues forming a tapered distal tip is provided and constitutes the distal end 103 of the tube 101. The advantage of closing the distal end 103 of the tube 101 by a tongue closure is that the tongue closure can be opened by a pushing force applied to the AM element 10 only. This is due to the bendability of the tongues of the tongue closure. No additional opening means for opening the closure are necessary. Closing the distal end 103 of the tube 101 also protects the AM element 10 from potential contamination until its release from the tube.

In a preferred embodiment, at least one of the tongues of the tongue closure, when compared with at least one other tongue, has a greater bending stiffness away from the longitudinal axis thereby forming the deflector 110. The tongue closure design allows the deflector 110 to be integrated within the closure by including at least one tongue that is less flexible than the other tongues, i.e., by including at least one tongue that has a greater bending stiffness when compared to the other tongues. This will lead to deflection of the AM element 10 during release of the AM element through the opening at the distal end 103 of the tube.

In another preferred embodiment, the deflector 110 is a release opening or exit opening located in a side wall of the tube 101 at a distal end portion of the tube. The release opening is configured to be passed by the AM element 10 during the release process of the AM element. Because the release opening is located in the side wall of the tube 101 in this embodiment, pushing the AM element 10 through the release opening causes the AM element to bend and therefore to deflect from the longitudinal axis of the tube 101.

The release opening is preferably closed until the AM element 10 is to be released. This protects the AM element 10 from potential contamination until its release from the tube 101.

The release opening is preferably closed by a tongue closure comprising a plurality of tongues. The advantage of closing the release opening of the tube 101 by a tongue closure is that the tongue closure can be opened by a pushing force applied to the AM element 10 only. This is due to a bendability of the tongues of the tongue closure. No additional opening means for opening the closure is necessary. Closing the release opening of the tube 101 also protects the AM element 10 from potential contamination until its release from the tube 101.

In another embodiment, the release opening is a through hole located in the side wall of the tube 101 at the distal end portion of the tube 101.

In one embodiment, the release element 106 is a piston type rod having a piston portion that is slidably mounted within the tube 101. Forming the release element 106 as a piston type rod allows pushing and releasing the AM element 10. The application device 100 has a latch mechanism that provides haptic feedback to the operator upon complete release of the AM element 10. For example, the tube 101 has a snap-in point into which the release element 106 snaps when the piston portion 107 has completely pushed the AM element 10 out of the release opening 105.

In another preferred embodiment, the release element 106 is a push rod reaching through a longitudinal side slot 150 of the tube 101. The push rod 151 is slidably movable along the slot 150. By moving the push rod 151 along the slot 150, the AM element 10 is moved forward, and push forces are applied to the AM element. This leads to the release of the AM element. Because there is no risk of kinking of the AM element 10 upon using the push rod, a soft AM element can be used.

In a preferred embodiment, the AM element 10 has a ribbon or leash 13 attached at its proximal end 12 for removing the AM element from its target position within the cavity. The ribbon or leash 13 facilitates the removal of the AM element from the cavity. Of advantage, the removal can be performed without contacting the absorptive matrix itself. The ribbon or leash 13 renders the removal process smooth and easy, thereby increasing the comfort of the patient.

In one embodiment, the ribbon or leash 13 unfolds when the tube 101 is removed from the cavity after the release of the AM element 10. The ribbon or leash unfolds along a removal route of the tube 101. This ensures that the ribbon or leash will extend to the entrance of the cavity so that the AM element 10 can be removed from the cavity by pulling at the ribbon or leash 13. The removal route of the tube 101 will generally be the same route as used for its insertion into the cavity.

In another embodiment, the leash 13 passes from the proximal end 12 of the AM element 10 out through the release opening and then essentially along the outside of the tube 101 towards the proximal end 104 of the tube. The leash 13 extends beyond the proximal end of the tube 101 and is held by a notch located on the outer surface of the application device in a region of the proximal end 104. In this embodiment, when the AM element 10 exits the tube 101, the leash 13 is already outside the tube 11 and does not need to pass through the tube 101 as the application device 100 is removed from the cavity.

In a preferred embodiment, a radiopaque marker is attached to the AM element 10, for example, in the form of a stripe or a dot. The radiopaque marker facilitates detecting the AM element 10 in case it becomes misplaced or undesirably lodged in the cavity.

In a preferred embodiment, the application device 100 comprises an illuminating means 118 capable of illuminating the cavity of the human or animal body during an insertion process of the application device and/or during a release process of the AM element 10. Illuminating the cavity facilitates a correct and reproducible positioning of the application device 100 as well as monitoring the release of the AM element 10. In this way, the illuminating device 118 also facilitates a correct and reproducible positioning of the AM element 10 at its intended target position within the cavity.

In a preferred embodiment, at least the tube 101 is tapered along at least a portion of its longitudinal dimension, wherein the tapering tapers towards the distal end 103 of the tube 101. Accordingly, the circumference of the proximal end 104 of the tube 101 is larger than the circumference of the distal end 103 of the tube 101. Tapering the tube 101 and/or the complete application device 100 towards its distal end 103 facilitates the insertion process of the application device into the cavity, especially in case the cavity is narrow. For example, in case the AM element 10 is to be positioned in the region of the olfactory cleft within the nasal cavity, the anatomical surrounding that needs to be passed by the application device 100 gets narrower towards the target position of the AM element 10. Tapering at least the tube 101 towards its distal end 103 facilitates finding an appropriate route of inserting the device while minimizing the risk of injury to the patient and improving the patient's comfort.

In a preferred embodiment, a latch mechanism is provided at a latching position, where the AM element 10 is released capable of latching the release element 106. The latch mechanism provides a haptic and acoustic feedback to the operator of the application device 100, the feedback indicating that the AM element 10 is completely released. This increases the safety of the patient, in particular in case the operator cannot visually confirm the complete release of the AM element. In case the release element 106 is a piston type rod having a piston portion that is slidably mounted within the tube 101, the AM element 10 preferably is released capable of latching the piston portion of the release element 106. Upon complete release of the AM element, the piston portion may, for example, engage in a recess arranged within the tube 101, the engagement being accompanied by an acoustic signal such as a click sound (acoustic feedback to the operator). After engaging in the recess, the piston portion can no longer be moved (haptic feedback to the operator). This also ensures that the pushing portion cannot be moved further forward, thereby increasing the safety of the patient.

In a preferred embodiment, a screw threading that protrudes from the inner circumferential surface of the tube 101 is provided that acts upon the AM element 10 to rotate the AM element along its longitudinal axis as the AM element 10 is pushed out of the tube 101. The internal screw threading or, alternatively, internal snakelike wound ribs cause the AM element 10 to rotate around its longitudinal axis during its release from the tube 101, thereby facilitating the positioning of the AM element by a drill-like rotation of the AM element. The rotation of the AM element 10 facilitates the positioning of the AM element at its intended target position.

In a preferred embodiment, a first portion of the tube 101 has an increased deformability when compared to a second portion of the tube 101, wherein the first portion is intended to be inserted into the cavity, and the second portion is not intended to be inserted into the cavity. In line with that, in a preferred embodiment, the deformability of the tube 101 at its distal end 103 is greater than the deformability of the tube 101 at its proximal end 104. The different levels of deformability render the insertion process of the application device 100 more comfortable for both the operator of the device and the patient.

In a preferred embodiment, wing-like plate elements 116 protrude from the outer circumferential surface of the tube 101 in a region of the proximal end 104 of the tube 101. The plate elements 116 allow the operator to dose/meter the application force applied to the release element 106 in a more sensitive manner. In one embodiment, the wing-like plate elements form a finger flange. In this way, the speed of the release process of the AM element 10 can be more easily controlled. This decreases the risk of inconvenience to the patient, which may be caused by a rapid release of the AM element.

In case the application device 100 is intended for collecting nasal secretion, the wing-like plate elements preferably have a total dimension that is larger than the entrance of a nostril so that the wing-like plate elements also serve as stoppage means that limits the insertion depth of the tube 101 in the nasal cavity. This decreases the risk of injury of the patient, such as an injury to the base of the skull.

In a preferred embodiment, one or a plurality of rotational marks are provided on the outer circumferential surface of the tube 101 or visible from the outside of the tube, wherein the at least one rotational mark is located such that when the device is positioned correctly with respect to its rotational axis in the nasal cavity, at least one rotational mark is configured to be directed to the forehead or to the chin or to the nasal septum. The rotational mark allows the operator of the device to control the correct positioning of the device within the nasal cavity before initiating the release process of the AM element 10.

In a preferred embodiment, the AM element 10 has an elongated shape.

In a preferred embodiment, the AM element 10 has a circular, oval or a polygonal cross-sectional shape having rounded edges in case of a polygonal cross-sectional shape. A polygonal cross-sectional shape having rounded edges decreases the risk of rolling-up of the AM element. It also decreases the risk of any kind of injury during the release of the AM element from the tube 101 and/or during absorption. A preferred polygonal cross-sectional shape having rounded edges is a triangular cross-sectional shape having rounded edges.

In case the tube 101 is provided with the screw thread protruding from the inner circumferential surface of the tube, an AM element 10 having a polygonal cross-sectional shape is preferred because it can be gripped more easily by the screw thread. This increases the reliability of the rotation of the AM element during the release process of the AM element.

In a preferred embodiment, the AM element 10 has a constant cross-sectional shape along its longitudinal axis or is tapered towards the distal end 11 of the AM element. In both cases, the distal end 11 and the proximal end 12 of the AM element 10 are preferably rounded. The tapered design of the distal end 11 of the AM element facilitates the positioning of the AM element at its intended target position. It also decreases the risk of any kind of injury during the release of the AM element from the tube 101.

In a preferred embodiment, the AM element 10 is made of an elastic and compressible material. The material may be a fibrous matrix. The material needs to be suitable for collecting secretion for subsequent analysis. Examples of suitable materials comprise nylon flocked, cellulose, cotton, a natural sponge material (such as a sponge material made from natural cellulose), a synthetic sponge material (such as a sponge material made from polyvinyl alcohol, hydroxylated polyvinyl acetate and/or polyurethane) and/or a foam material (such as a foam material made from fiber polymers).

In a preferred embodiment, the AM element 10 has a length of about 2 cm to 6 cm and a diameter of about 2 mm to 6 mm. As described above, the AM element is preferably tapered towards its distal end 11. In this case, the smallest diameter of the AM element, at a distal end portion of the AM element, is preferably about 2 mm, and the largest diameter of the AM element, at a proximal end 12 portion of the AM element, is preferably about 3 mm to 6 mm.

Figure 3B:
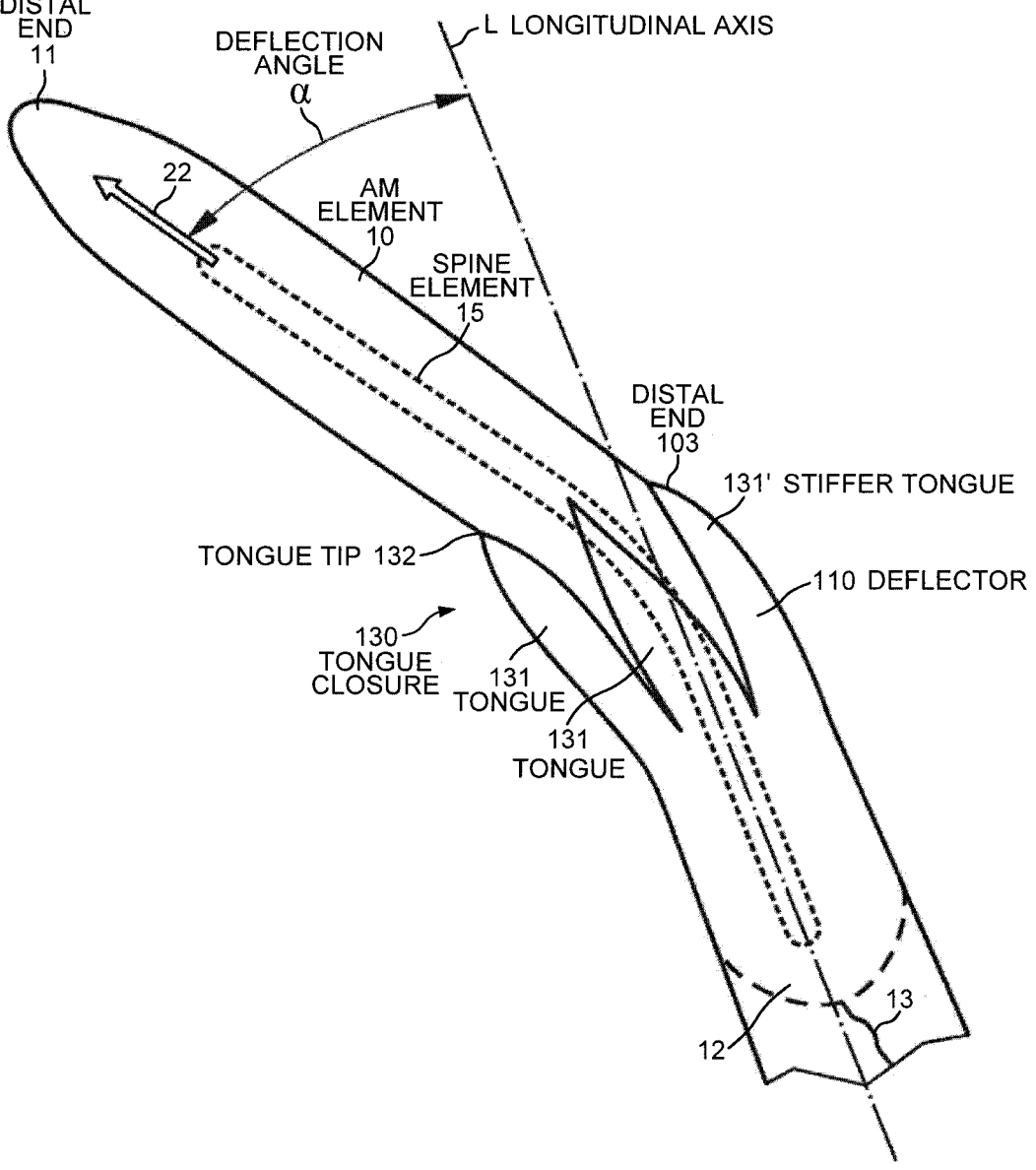
FIG. 3B shows an enlarged view of the detailed area Y in FIG. 3A.

FIG. 3B shows a preferred embodiment in which the AM element 10 is at least partially stiffened against kinking. To this end, the AM element 10 has a spine element 15 at least along a portion of its longitudinal dimension, wherein the spine element is bendable but not kinkable within the estimated range of push forces applied to the AM element 10 during its release from the tube 101. The spine element 15 increases the kinking stiffness of the AM element 10 while maintaining the bendability of the AM element along its extension direction. In this way, the spine element 15 allows the movement of the AM element 10 to be more accurately defined during the release process and to render the movement more predictable. The spine element 15 is further helpful with respect to avoiding an agglomeration or lumping or rolling-up of the AM element 10 within the storage and release tube 101 caused by pushing forces applied to the AM element during the release process. This facilitates the positioning of the AM element 10 at its target position in a stretched form. The spine element 15 can be arranged, for example, within the AM element 10 (such as at the center of the AM element) or on one or more sides of the AM element. In case of a polygonal AM element 10, the spine element can be arranged, for example, on each polygonal side.

In a preferred embodiment, as an additional safeguard for the patient, the AM element 10 is surrounded by a thin stretchable mesh or layer for preventing residues of the AM element from remaining in the cavity upon removal of the AM element from the cavity. The mesh or layer ensures the physical integrity of the AM element 10. The mesh or layer is designed so that it does not significantly reduce the absorptive surface of the AM element.

Figures 5, 6:
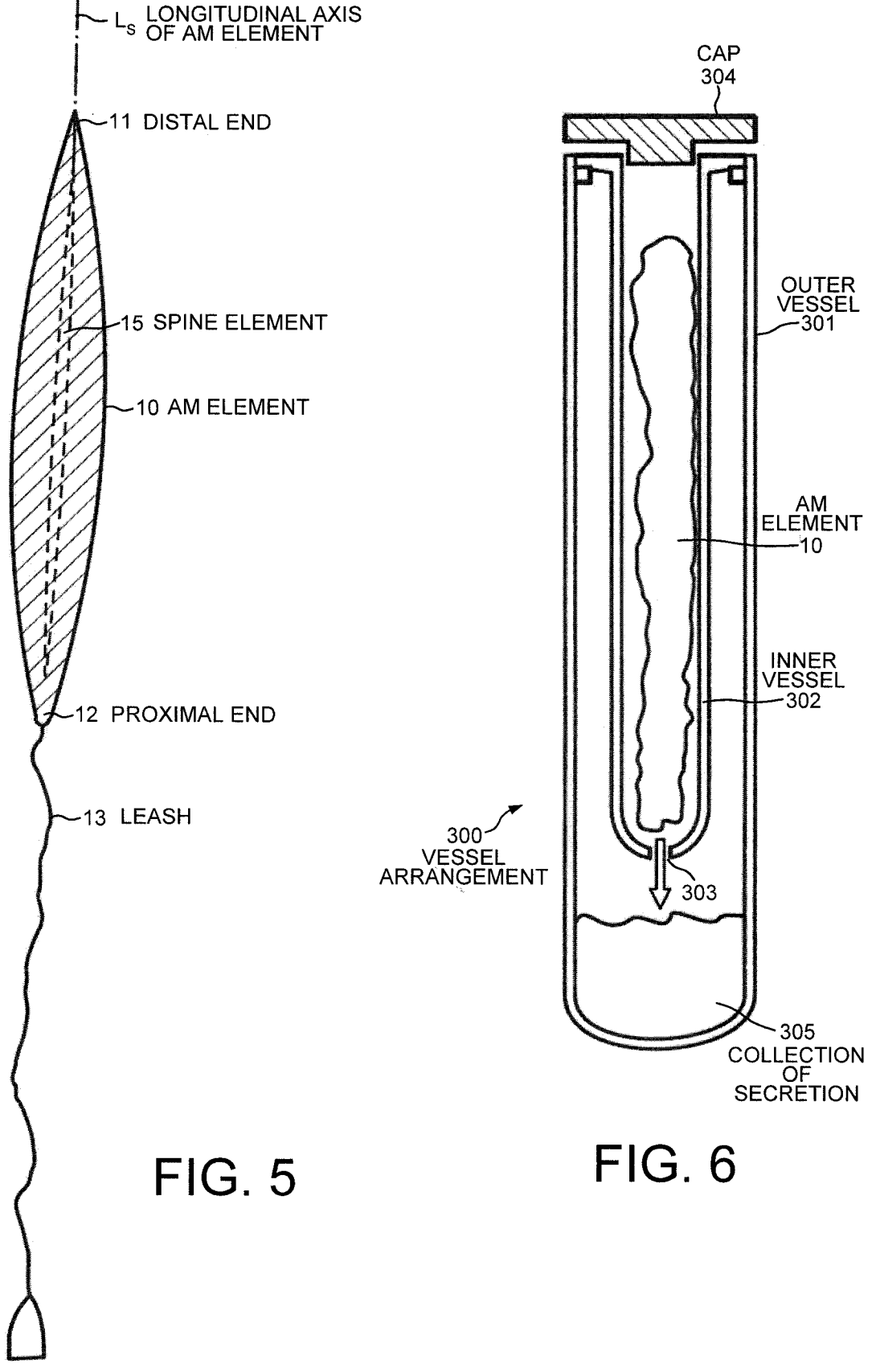
FIG. 5 shows an embodiment of an AM element suitable for the application device according to the invention.
FIG. 6 shows a cross sectional view of a vessel arrangement suitable for storing and/or transporting an AM element after the collection of secretion.

A second aspect of the present invention is illustrated in FIG. 6, which involves a collection kit for collecting biological secretions from a cavity of a human or animal body, the collection kit comprising the application device 100 as well as a vessel arrangement 300 for storing the AM element 10 after the collection of secretion.

The collection kit preferably is applicable for collecting nasal secretions, in particular nasal secretions from a region above the nasal turbinates, in particular nasal secretions from the olfactory cleft.

The vessel arrangement 300 preferably is configured to fit into a centrifugal device for centrifugation of the AM element 10. Centrifugation of the AM element is an efficient way of recovering the secretion from the AM element for further analysis. Providing a vessel arrangement configured to fit into a centrifugal device eliminates a transfer step for transferring the AM element 10 from a transport vessel to a centrifuge vessel. Elimination of the transfer step saves time and material and reduces the risk of contamination of the sample. It also reduces the risk of loss of sampling material.

In a preferred embodiment, the vessel arrangement comprises an inner vessel 302 and an outer vessel 301, wherein the inner vessel is configured to receive the AM element 10 after collection of secretion and has at least one opening 303 such that an inner space of the inner vessel 302 communicates with an inner space of the outer vessel 301. The inner vessel has a smaller diameter compared to the outer vessel and has a shorter length compared to the outer vessel, such that the inner vessel is completely insertable within the outer vessel. Such a two-shell design of the vessel arrangement 300 having an inner vessel (smaller vessel) and an outer vessel (larger vessel) facilitates the further processing of the AM element 10 by centrifugation. The outer vessel 301 is configured to fit into a centrifugal device. During centrifugation, the AM element 10 remains in the inner space of the inner vessel 302 while the secretion separates from the AM element and locates to the inner space of the outer vessel 301.

In a preferred embodiment, the inner vessel 302 is insertable into and lockable with respect to the outer vessel 301 of the vessel arrangement 300. In this way, a defined mechanical fixation of the inner vessel in relation to the outer vessel is ensured.

Nasal secretions are preferably collected from each of the left nasal cavity and the right nasal cavity of a patient. After collection, the secretion of the left nasal cavity and the secretion of the right nasal cavity preferably are combined for further analysis. To this end, the vessel arrangement 300 preferably is configured to store two AM elements in the same vessel after the collection of secretion. In this case, the secretion collected by the two AM elements 10 can be easily combined during the recovery of the secretions from the two AM elements, for example by centrifugation. In this case, it is not necessary to transfer any of the secretions from one vessel to another vessel in order to combine the secretions of the two AM elements. In this way, a potential loss of the secretion sample is prevented.

The vessels of the vessel arrangement 300 are generally made of a material that is low-binding and/or non-absorptive with respect to proteins and other analytes. The vessels can be made of, for example, glass, polyethylene or polypropylene.

In a third aspect, the present invention relates to the use of the application device 100 of the invention or the collection kit of the invention for collecting nasal secretion, in particular for collecting nasal secretion from the olfactory cleft.

The present disclosure further relates to an application device applicable for positioning an absorptive matrix (AM) element within a cavity of a human or animal body, the application device comprising:

a storage and release tube having a distal end and a proximal end, the tube being configured to store and release an AM element;

a release element being slidably supported with respect to the tube along a longitudinal axis of the tube, the release element being configured to release the AM element from the tube;

at least one deflector arranged at the distal end of the tube, the deflector being capable of bending the AM element away from the longitudinal axis of the tube when the AM element is released from the tube.

The application device 100 of the disclosure can be filled with an AM element 10. The AM element 10 is to be positioned within an inner space of the tube 101.

The features, advantages and preferred embodiments of the application device 100 of the invention as described above likewise apply to the application device of the disclosure.

The present disclosure further relates to an application kit applicable for positioning an AM element 10 within a cavity of a human or animal body, the application kit comprising the application device 100 of the disclosure and at least one AM element 10 configured to be insertable into an inner space of the tube 101.

The present disclosure further relates to a collection kit applicable for collecting biological secretion from a cavity of a human or animal body comprising the application device 100 of the disclosure, wherein the collection kit further comprises a vessel arrangement for storing the AM element 10 after the collection of secretion.

In a third aspect, the present disclosure relates to the use of the application device 100 of the disclosure or the collection kit of the disclosure for collecting nasal secretion.

The features, advantages and preferred embodiments of the collection kit of the invention as described above likewise apply to the collection kit of the disclosure. The same applies to the use of the application device 100 of the disclosure or the collection kit of the disclosure.

Figure 1:
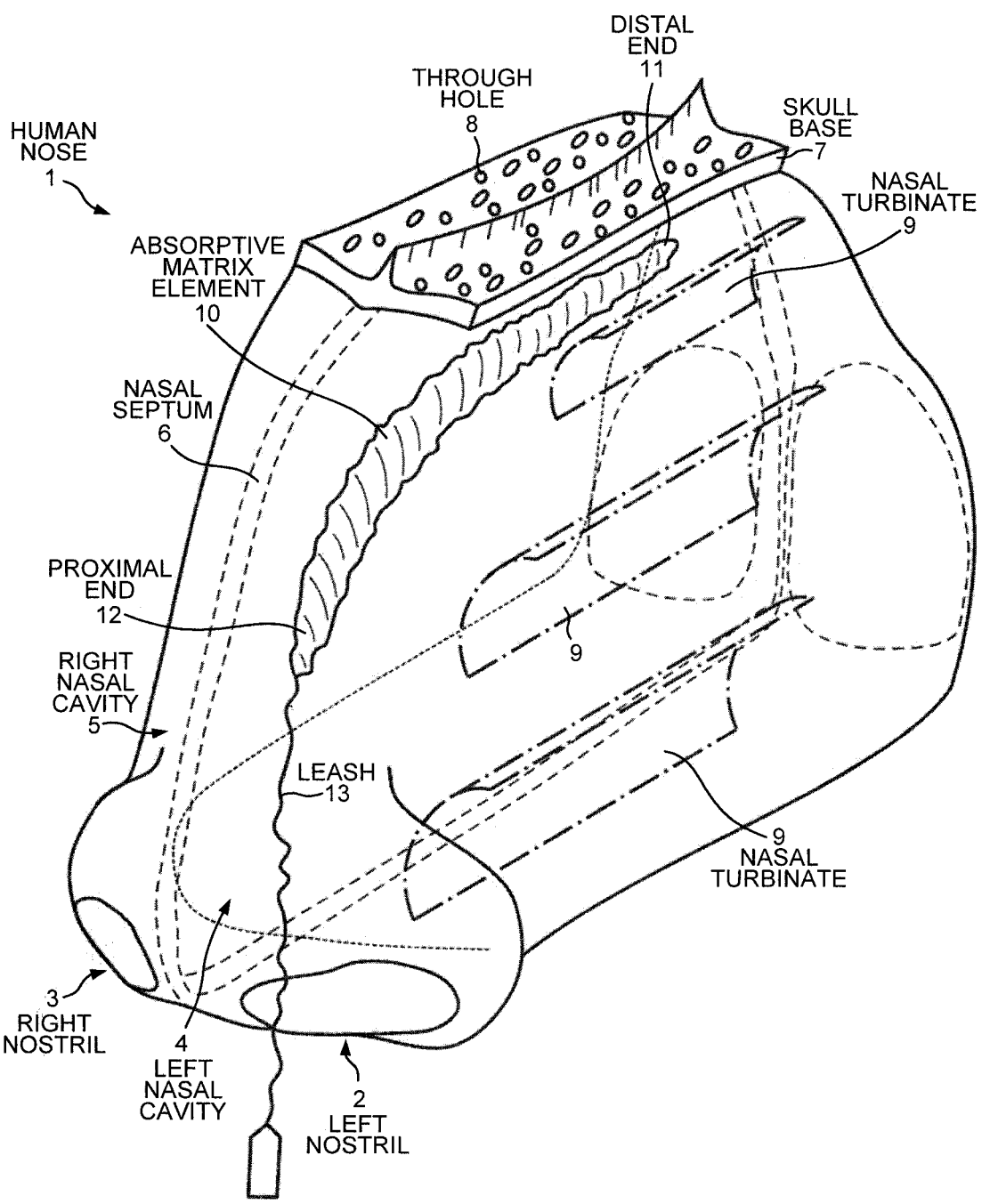
FIG. 1 shows a perspective view of a human nasal cavity in which an AM element has been released for collecting secretion. The perspective view is shown in a semitransparent manner.

FIG. 1 shows a perspective view of a human nose 1. The perspective view is shown in a semitransparent manner. The human nose 1 has a left nostril 2 and a right nostril 3. Corresponding to the nostrils 2-3 there is a left nasal cavity 4 and a right nasal cavity 5. The nasal cavities 4-5 are separated by a nasal septum 6. The nasal cavities 4-5 are covered by mucosa. At an upper end of the nasal cavities 4-5 there is a skull base 7, which separates the nasal cavities 4-5 from an inner space of the skull. In some parts, the skull base 7 is made of very thin bone material and has a porous structure, having a plurality of through holes 8, through which olfactory fibers (not shown) protrude into the upper region of the nasal cavities 4-5.

Three nasal turbinates 9 are located opposite to the nasal septum 6 in each nasal cavity 4-5. For collecting nasal secretion from an olfactory cleft that is located in the vicinity of the skull base 7, an absorptive matrix (AM) element 10 is positioned in the olfactory cleft, i.e., in the narrow space between the skull base 7, the nasal septum 6 and the uppermost nasal turbinate 9, medial to the uppermost nasal turbinate 9 and just below the skull base 7. This region of the nasal cavity 4-5 is difficult to reach from the nostrils 2-3 by an instrument or a device. The AM element 10 has been positioned in the olfactory cleft by release from an application device (not shown in FIG. 1). The application device 100 has already been removed.

Given that the amount of nasal secretion is very low, a long collection time, which corresponds to a long residence time of the AM element 10 below the skull base 7, such as, for example, fifteen minutes, is needed in order to collect a sufficient amount of nasal secretion for subsequent analysis.

The AM element 10 has a distal end 11 and a proximal end 12. A leash 13 is attached to the proximal end 12 of the AM element 10 or at least towards the proximal end 12. The leash 13 allows the AM element 10 to be pulled out from its absorption position shown in FIG. 1 to remove the AM element 10 from the nasal cavity 4-5, passing the respective nostril 2-3.

In the position of the AM element 10 shown in FIG. 1, the distal portion of the AM element 10 is essentially arranged in a horizontal direction below the skull base 7, and the proximal portion of the AM element 10 bends to a nearly vertical direction with respect to its distal portion. The proximal portion of the AM element 10 is located such that the proximal end 12 is essentially directed towards the respective nostril 2-3.

Several embodiments of the application device 100 will now be described with reference to FIGS. 2A, 2B, 3A, 3B and 4.

A first embodiment of the application device 100 will now be described with respect to FIGS. 2A-2B.

The application device 100 has a storage and release tube 101, which is configured to store an AM element 10 within an inner space 102 of the storage and release tube 101. The storage and release tube 101 has a distal end 103 and a proximal end 104. The storage and release tube 101 has a longitudinal axis L.

At the distal end 103, the storage and release tube 101 has a release opening or exit opening 105, through which the AM element 10 can be pushed out of the inner space 102 by a release element 106. The release element 106 is a piston type rod and has a piston portion 107 and a push rod portion 108. The piston portion 107 is slidably mounted within the inner space 102 of the storage and release tube 101. The piston portion 107 is configured to be able to push against the proximal end 12 of the AM element 10, thereby pushing the AM element 10 through the release opening 105 out of the storage and release tube 101.

In one aspect, the piston portion 107 is provided with an opening (not shown) to enable the leash 13 to pass through the opening from the inner space 102 of the storage and release tube 101 to the outside thereof. In another aspect, the leash 13 passes from the proximal end 12 of the AM element 10, out through the exit opening 105 and back along the outside of the tube 101 and past the proximal end 104 of the tube 101.

The release opening 105 is located in the region of the distal end 103 of the storage and release tube 101. A wall portion 109 is protruding from the distal end 103 of the storage and release tube 101. The wall portion 109 is formed in a manner such that it is inclined with respect to the longitudinal axis L towards the longitudinal axis L. In this way, the wall portion 109 acts as a deflection means or deflector 110, which causes the AM element 10 to bend away from the longitudinal axis L of the storage and release tube 101 when the AM element 10 is released from the storage and release tube 101.

The AM element 10 is not fixedly attached to any of the tube 101, the release element 106 or the deflector 110.

The application device 100 with the AM element 10 being stored within the storage and release tube 101 can be inserted into one of the nasal cavities 4-5. During insertion, the storage and release tube 101 does not necessarily need to be bent. When inserting the storage and release tube 101 far enough into one of the nasal cavities 4-5, the AM element 10 can be released in a protruding movement to the desired target region below the skull base 7 and medial to the uppermost nasal turbinate 9 by bending of the AM element 10. The AM element 10 is caused to bent by the deflector 110, which is a protruding (extended) wall portion 109 that bends the AM element 10 during its release through release opening 105.

In order to avoid injuries of the mucosa, a shroud means 112 is provided in a transition region 111 of the storage and release tube 101 close to its distal end 103. The shroud means 112 comprises at least two cushion elements 113, which are arranged along an outer circumferential surface 114 of the storage and release tube 101, more specifically along the outer circumferential surface of the transition region 111.

Further, a scale of marks 115 is provided on the outer circumferential surface 114 of the storage and release tube 101 or at least visible from the outside of the storage and release tube 101. The scale of marks 115 is provided along a longitudinal direction 20 of the storage and release tube 101. The scale of marks 115 indicates the insertion depth of the storage and release tube 101 into the cavity of the human or animal body, in particular into the nasal cavity 4-5. The scale of marks 115 helps the operator of the application device to estimate the position of the distal end 103 of the storage and release tube 101 for releasing the AM element 10 to the intended target position.

Further, at least one plate element 116 may be provided at the proximal end 104 of the storage and release tube 101. The plate element 116 protrudes radially outward from the outer circumferential surface 114 and acts as a support means for the operator for a better holding of the application device 100 during the positioning of the AM element 10. Two oppositely protruding plate elements 116 can be formed as a finger flange to be grasped by two fingers of the operator so that the operator can press in the push rod 108 with the operator's thumb.

Additionally, at least one rotational mark 117 may be provided on the outer circumferential surface of the storage and release tube 101 or at least visible from the outside of the storage and release tube 101 in order to facilitate the correct positioning of the storage and release tube 101 within the nasal cavity 4-5 along a rotational direction 21. The rotational mark 117 may be positioned such that it corresponds to the opening direction of the release opening 105 and/or such that it is directed to the chin and/or the nasal septum 6 or another characteristic portion of the human or animal body, which helps to position the application device 100 correctly with respect to the intended target position of the AM element 10.

Furthermore, an illuminating device 118 may be integrated at a suitable position of the application device 100 in order to illuminate the cavity of the human or animal body, in particular the nasal cavity 4-5, during the release process of the AM element 10. Illuminating the cavity further facilitates the correct positioning of the AM element 10 at its intended target position.

In FIG. 2A, the application device 100 is shown in a state in which the AM element 10 is in its storage (retracted) position before its release and in a state in which the AM element 10 is in a partially released position, i.e., in which the AM element 10 has partially left the storage and release tube 101 and therefore passes through the release opening 105. In a state before the release of the AM element 10, it is preferred that the release opening 105 is closed by a closure (not shown in FIG. 2A) to avoid undesired contamination of the AM element 10 through the release opening 105 during its insertion into the cavity. The closure may be a film (not shown) attached to the release opening 105 by gluing or welding. It is preferred to configure the closure such that it can be pushed away or pushed open by the distal end 11 of the AM element 10 when the AM element 10 is pushed out of the storage and release tube 101. The film, for example a thin plastic sheet, needs to stay connected to the storage and release tube 101 after the AM element 10 has been pushed through the film so that the film does not get lost within the cavity.

Further, the storage and release tube 101 may be formed of a material which is stiffer when going to the proximal end 104 and which is more flexible/deformable when going to the distal end 103 in order to minimize injuries of the mucosa. The deflector 110, however, is of an increased stiffness, at least against bendability, in order to ensure the desired deflection of the AM element 10 away from the longitudinal axis L when the AM element 10 is released from the tube 101. To this end, the deflector 110 may be formed with an increased wall thickness, which increases the stiffness against bending. Additionally or alternatively, it is possible to design the deflector 110 in a bowl shape, which is a shape that comprises a higher stiffness against bending when compared to a flat plane design and is thus suitable to act as a deflector 110.

Another alternative is to form the deflector 110 of a material that has an increased stiffness and resistance against bending when compared to the bending stiffness of the AM element 10.

Figure 2B:
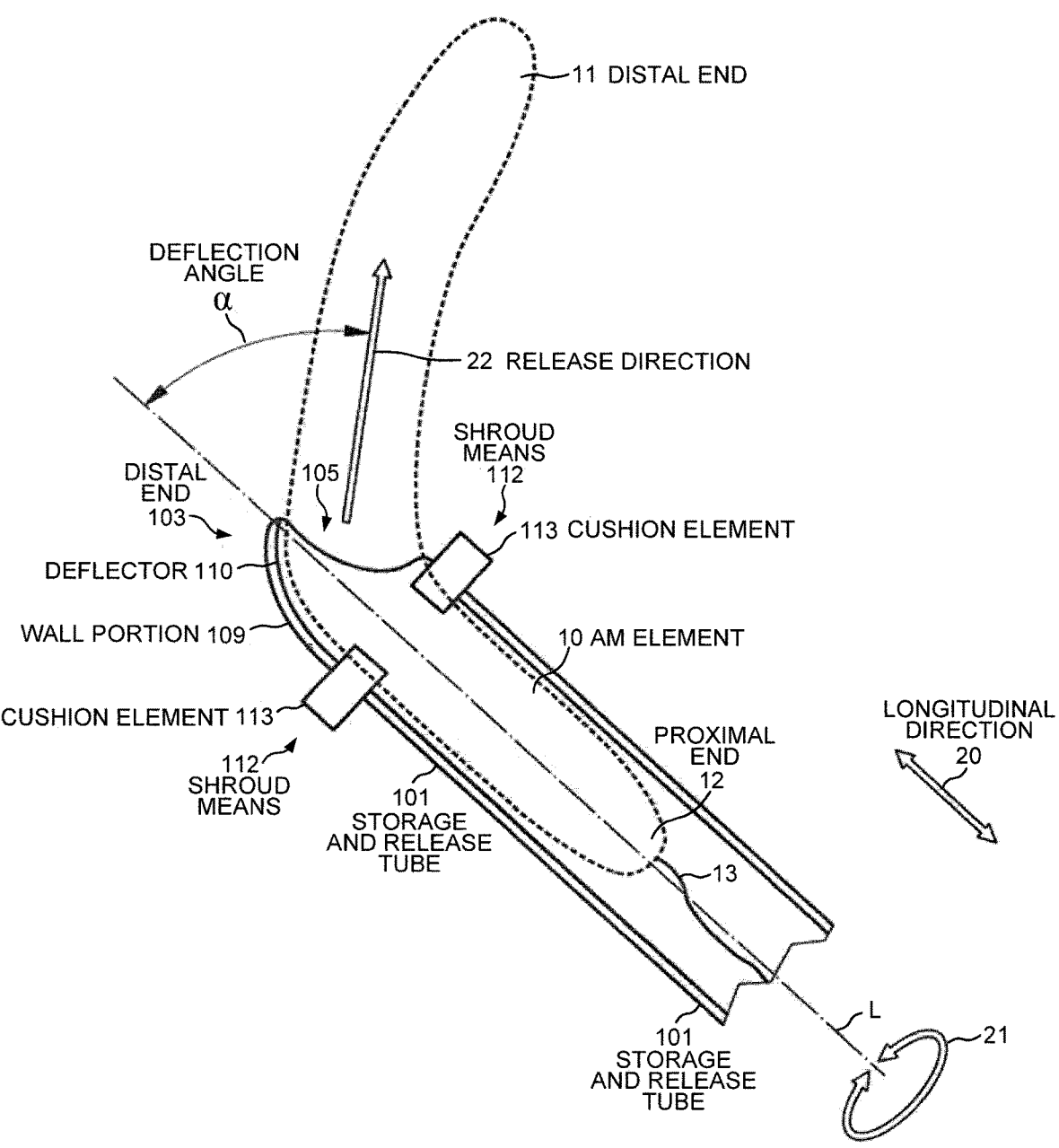
FIG. 2B shows an enlarged view of the detailed area X in FIG. 2A.

FIG. 2B shows an enlarged view of detailed area X shown in FIG. 2A. The deflection means or deflector 110 is formed by the extended wall portion 109 of the storage and release tube 101 protruding from the distal end 103 of the storage and release tube 101 and inclined with respect to the longitudinal axis L towards the longitudinal axis L.

It is to be understood that each element that causes a release direction 22 of the AM element 10 that is inclined with respect to the longitudinal axis L by a deflection angle α that is greater than 0° can be seen as a means for deflection, a deflection means or a deflector 110.

A second and third embodiment of the application device 100 will now be described with reference to FIGS. 3A, 3B and 4. Elements having the same function and/or the same location will be referred to with the same reference numerals. In order to avoid unnecessary replication, the embodiments of FIGS. 3A, 3B and 4 will only be described with respect to their differences between the second/third embodiment and the first embodiment described above. Statements regarding the function and/or the features of the first embodiment described above are also applicable to the embodiments described below and will therefore not be repeated.

In the embodiment shown in FIG. 3A, the closure is formed as a tongue closure 130, which is composed of a plurality of tongues 131. The tongues 131 each have a tongue tip 132, which is directed towards the distal end 103 of the storage and release tube 101. The plurality of tongue tips 132 constitute the distal end 103 of the storage and release tube 101. At least one of the tongues 131 is designed with a higher bending stiffness to and from the longitudinal axis L of the storage and release tube 101 when compared with the bending stiffness to and from the longitudinal axis L of the storage and release tube 101 of the other tongues 131.

The one or more tongues 131 that have a higher bending stiffness form the deflection element 110 as these tongues 131 of higher bending stiffness are not bent away or bent away to a smaller extent by the protruding AM element 10 during its release. In other words, the softer tongues 131, i.e., the tongues 131 having a lesser bending stiffness, are bent away from the longitudinal axis L when the AM element 10 is pushed through the tongue closure 130 during its release and therefore are of a lower resistance when compared to the stiffer tongues 131. As a result, the AM element 10 will be released from the storage and release tube 101 through the tongue closure 130 in a release direction 22 that is inclined with respect to the longitudinal axis L by the angle α. The release direction 22 also has the inclination (deflection) angle α of greater than 0° with respect to the longitudinal axis L. The degree of deflection can be influenced by selecting the degree of difference between the bending stiffness of the stiffer tongues 131 and the bending stiffness of the softer tongues 131.

A further way of influencing the stiffness of the tongues 131 is based on the length of the tongues 131 along the longitudinal direction 20 of the tongues 131. Shorter tongues 131 usually have a higher bending stiffness compared to longer tongues 131 made of the same material and the same geometry.

FIG. 3B shows an enlarged view of detailed area Y shown in FIG. 3A. The stiffer tongue 131' shown in FIG. 3B forms the deflector 110 as it is stiffer compared to the other tongues 131, which are bent away by the AM element 10 protruding through the tongue closure 130. Because of the difference in stiffness of the tongues 131, 131', the AM element 10 is bent away from the longitudinal axis L of the storage and release tube 101 when it is released from the storage and release tube 101 by a pushing movement of the piston portion 107.

A further feature shown in FIG. 3B is that the storage and release tube 101 is designed in a tapered way along its longitudinal dimension, tapering towards the distal end 103 of the tube 101. This is also applicable to the other embodiments described above or below.

In addition, the embodiment shown in FIG. 3A has a ring land 140, which serves as a stoppage land. The ring land 140 protrudes from the outer circumferential surface 114 of the storage and release tube 101 in the vicinity of the proximal end 104. The ring land 140 serves as a stoppage land which limits the insertion depth of the tube 101 into the cavity, avoiding an insertion that would be too far and thereby cause injuries.

To support the bendability of the AM element 10 and to avoid unintended kinking of the AM element 10, the AM element 10 may comprise a spine element 15. The spine element 15 renders the AM element 10 more rigid against kinking but can easily be bent by the deflector 110 such that the AM element 10 can be smoothly pushed out of the storage and release tube 101. Alternatively, instead of using a spine element to stiffen the AM element 10, the AM element 10 is made more rigid by tightly winding the absorptive matrix material of the AM element 10.

A third embodiment of the application device 100 will now be described with reference to FIG. 4.

The application device 100 of the third embodiment comprises a spreader device 200 having spreading arm means 201, which are connected to actuation arms 202. The actuation arms 202 are joined by a pivot 203 in a manner that when the actuation arms 202 are pushed together, the spreading arm means 201 are moved away from each other thereby spreading an opening into which the spreading arm means 201 are inserted (e.g., an opening of the nasal cavity 4-5).

Figure 4:
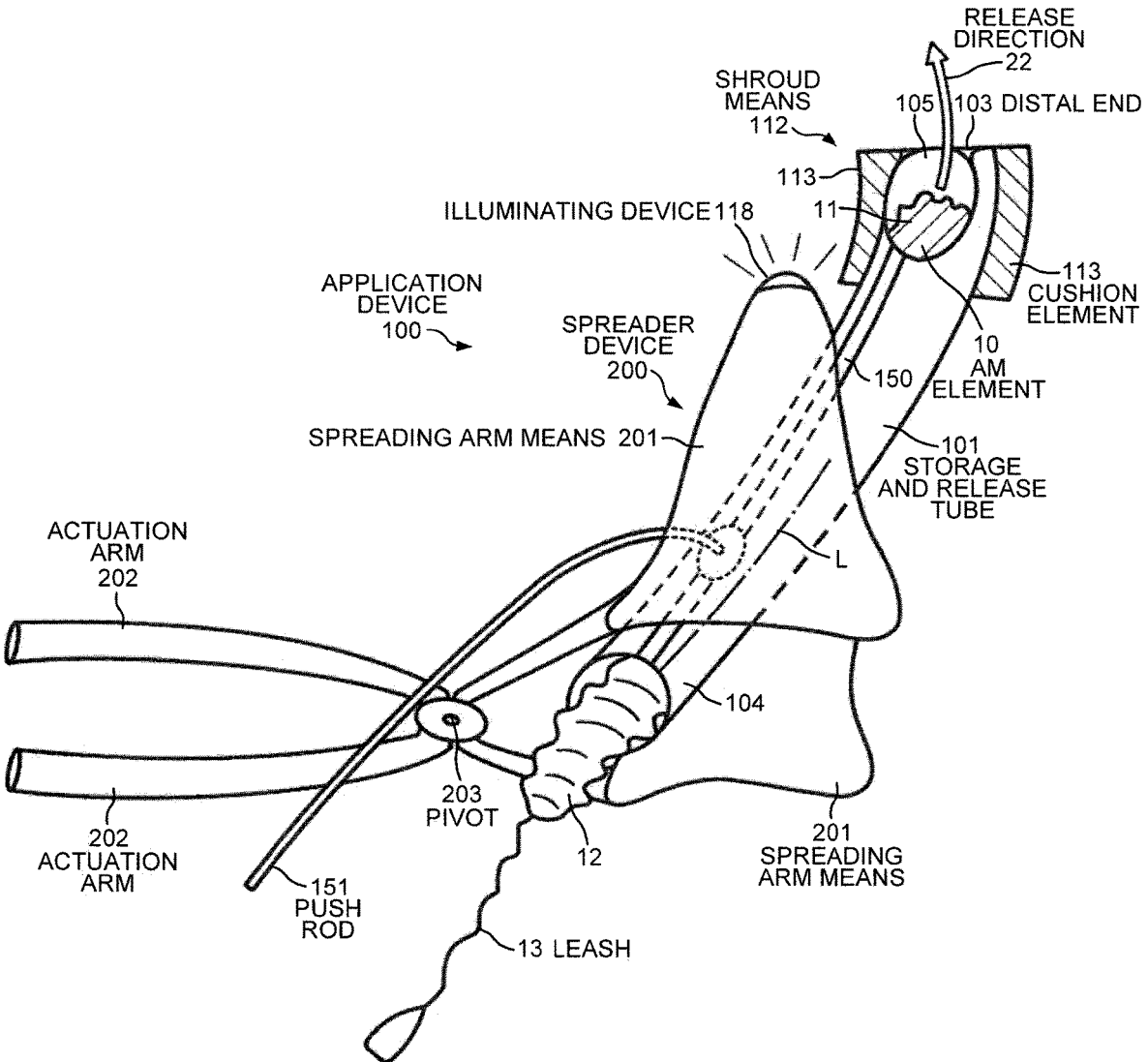
FIG. 4 shows a perspective view of a third embodiment of an application device according to the invention with an AM element in its storage (retracted) position.

The embodiment of the application device 100 shown in FIG. 4 further differs from the embodiments described above by a longitudinal side slot 150 extending at least partially over the longitudinal direction 20 of the storage and release tube 101. Within the longitudinal side slot 150, a push rod 151 is slidably mounted such that the push rod 151 can be moved along the longitudinal side slot 150 by pushing it forward and backward.

One end of the push rod 151 extends into the inner space 102 of the storage and release tube 101 and acts on the AM element 10 that is stored within the storage and release tube 101. By pushing the push rod 151 towards the distal end 103 of the storage and release tube 101, it is possible to release the AM element 10 from the storage and release tube 101.

The additional features described above (spreader device 200, push rod 151 acting on the AM element 10 via a longitudinal side slot 150) are also applicable to the embodiments described above.

FIG. 5 shows an embodiment of an AM element 10 suitable for the application device 100. The AM element 10 has a distal end 11 and a proximal end 12. The leash 13 is attached to the proximal end 12. Additionally, the AM element 10 has the spine element 15 located at the center, thereby representing the longitudinal axis $L_S$ of the AM element 10. The AM element 10 is made of a material that is capable of absorbing secretion such as nasal secretion. In order to stiffen the material of the AM element 10 against kinking, the spine element 15 is provided. The spine element 15 has a sufficient stiffness against kinking while being sufficiently bendable by the deflector 110 of the application device 100.

The spine element 15 may alternatively be located on one or more sides of the AM element, for example, in case of a polygonal AM element, on each polygonal side.

All of the embodiments described above may additionally comprise a screw thread protruding inwards from an inner circumferential surface of the storage and release tube 101. The screw thread (not shown) may have a spiral-like winding along the inner circumferential surface and may interact with the AM element 10 during its release, thereby causing the AM element 10 to rotate in the rotational direction 21 along its longitudinal axis $L_S$ during the release process of the AM element 10. This measure facilitates the release of the AM element 10 as it acts like a drill during its movement to the desired target position.

FIG. 6 shows a cross sectional view of a vessel arrangement 300 that will now be described. The vessel arrangement 300 is suitable for safely storing and/or transporting an AM element 10 after the collection of secretion 305. The vessel arrangement 300 is part of an embodiment of the collection kit, the collection kit comprising the application device 100 and the vessel arrangement 300 for storing the AM element 10 after the collection of secretion 305.

The vessel arrangement 300 is composed of an outer vessel 301 and an inner vessel 302. The inner vessel 302 has a smaller diameter compared to the outer vessel 301 and has a shorter length compared to the outer vessel 301, such that the inner vessel 302 is completely insertable within the outer vessel 301. After the collection of secretion, the AM element 10 can be stored within the inner vessel 302, which preferably has an inner diameter equal to or slightly greater than the outer diameter of the AM element 10.

In a preferred embodiment, the vessel arrangement comprises an inner vessel and an outer vessel, wherein the inner vessel is configured to receive the AM element after collection of secretion and has at least one opening 303 such that an inner space of the inner vessel communicates with an inner space of the outer vessel. Such a two shell design of the vessel arrangement having an inner vessel (smaller vessel) and an outer vessel (larger vessel) facilitates the further processing of the AM element 10 by centrifugation. The outer vessel 301 is configured to fit into a centrifugal device. During centrifugation, the AM element 10 remains in the inner space of the inner vessel 302 while the secretion separates from the AM element 10 and locates to the inner space of the outer vessel 301.

The inner vessel 302 has an opening 303 at its bottom end. The inner vessel 302 is arranged within the outer vessel 301. Both of the vessels 301, 302 may be closed by a cap 304. The outer vessel 301 is preferably configured to fit into a rotating carousel of a centrifugal device. By centrifuging the vessel arrangement 300 comprising the AM element 10, the secretion 305 separates from the AM element 10 and passes through the opening 303 by centrifugal forces. The secretion 305 is thus collected at the bottom of the outer vessel 301 when the vessel arrangement 300 is exposed to centrifugal forces.

Figure 7:
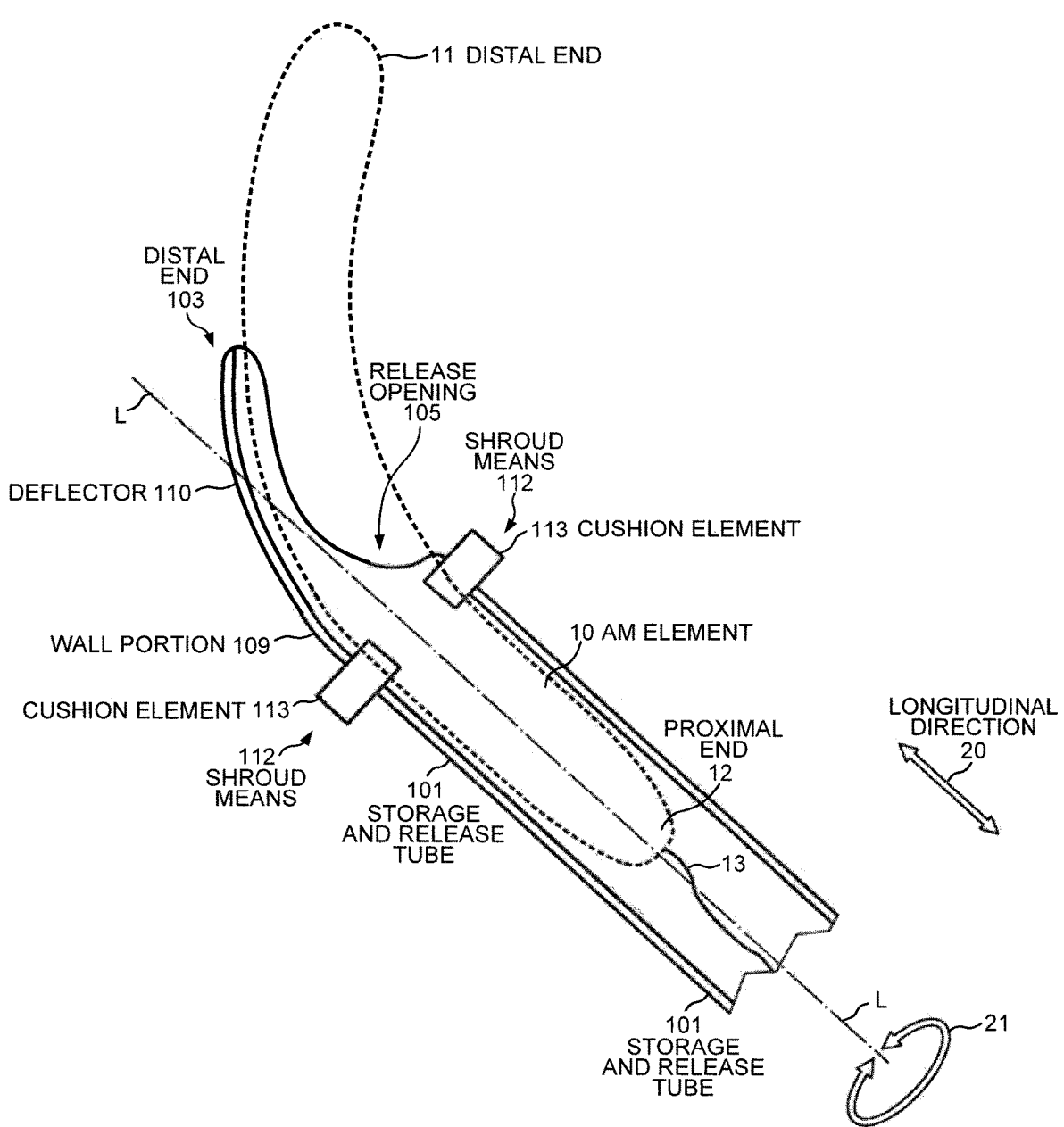
FIG. 7 shows another embodiment of an application device with a deflector at the distal end of the tube that bends inward towards the longitudinal axis of the tube.

FIG. 7 shows another embodiment of the application device 100 that has a deflector 110 at the distal end 103 of the tube 101 that bends inward towards and past the longitudinal axis L of the tube 101. The deflector 110 is formed by an extension of the wall of the tube 101 that protrudes on one side of the release opening 105. The deflector 110 of the embodiment of FIG. 7 is longer and more bent than the deflection means shown in the embodiment of FIGS. 2A-2B.

Figure 8:
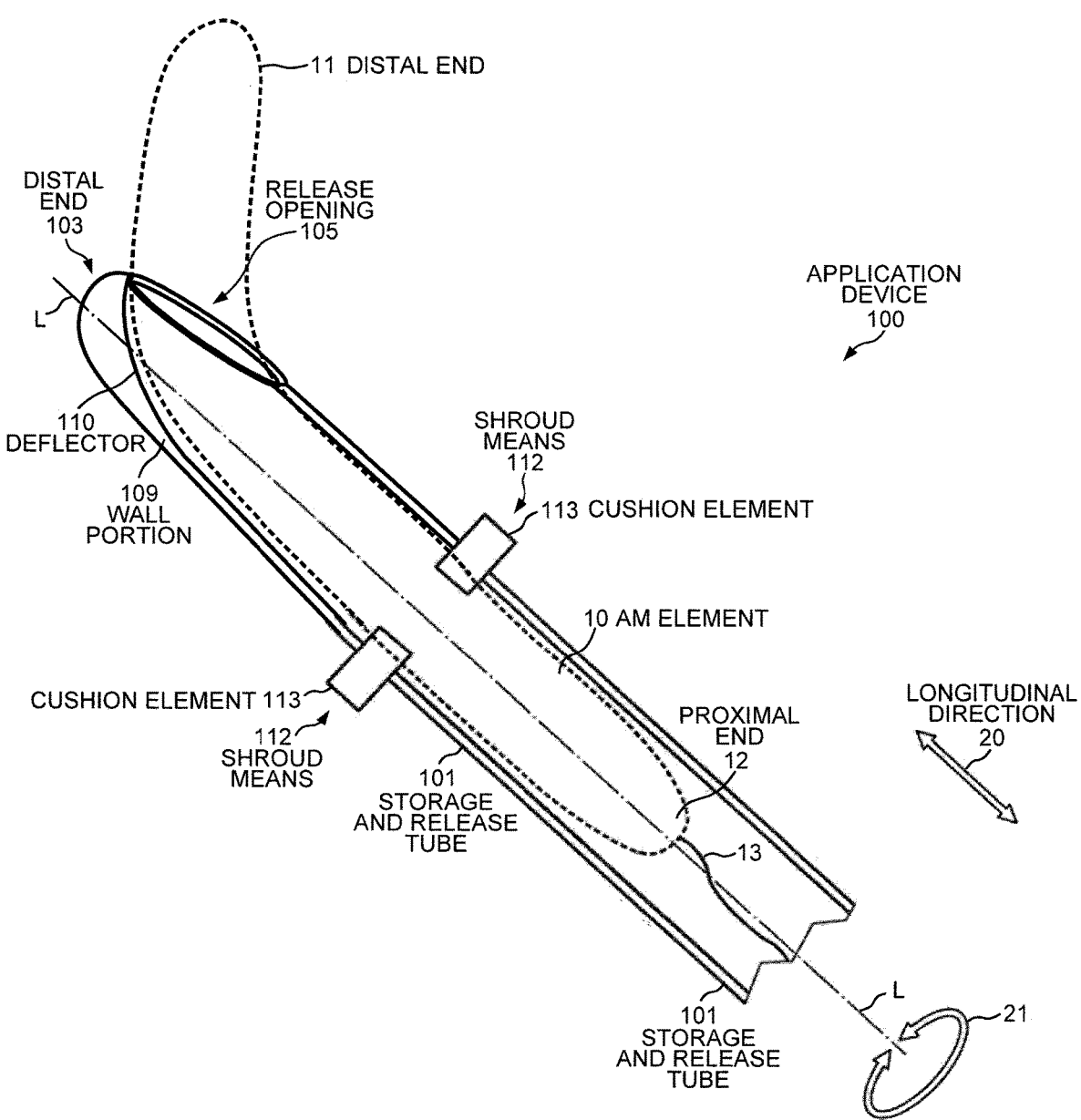
FIG. 8 shows yet another embodiment of an application device in which the release opening is in the tube wall towards the distal end.

FIG. 8 shows yet another embodiment of the application device 100 in which the release opening 105 is made through the wall of the tube 101 as opposed to through the end of the tube 101. In the embodiment of FIG. 8, the release opening 105 is an oval in the tube wall towards the distal end 103 of the tube 101. The deflector 110 is formed by a thickened part of the wall portion 109 near the distal end 103. The wall portion 109 is formed such that its inner surface is inclined with respect to the longitudinal axis L of the storage and release tube 101. The deflector 110 causes the AM element 10 to bend away from the longitudinal axis L of the tube 101 as the AM element 10 is pushed out of the release opening 105.

The tube 101 has a rounded distal end 103, which reduces the chances of injuring the patient as the application device 100 is inserted into the patient's nostril. The distal end 103 of the tube 101 is preferably made of a soft, rubberlike material. The tube 101 is also tapered towards the distal end 103, which enables easier and more accurate access into the patient's olfactory cleft.

REFERENCE NUMERALS

1 human nose
2 left nostril
3 right nostril
4 left nasal cavity
5 right nasal cavity
6 nasal septum
7 skull base
8 through holes
9 nasal turbinate
10 AM element
11 distal end (of the AM element)
12 proximal end (of the AM element)
13 leash
15 spine element
20 longitudinal direction
21 rotational direction
22 release direction
100 application device
101 storage and release tube
102 inner space
103 distal end
104 proximal end
105 release opening
106 release element
107 piston portion
108 push rod portion
109 wall portion
110 deflector
111 transition region
112 shroud means
113 cushion element
114 outer circumferential surface
115 scale of marks
116 plate element
117 rotational mark
118 illuminating device
130 tongue closure
131 tongue
131' stiffer tongue
132 tongue tip
140 ring land
150 longitudinal side slot
151 push rod
200 spreader device
201 spreading arm means
202 actuation arms
203 pivot
300 vessel arrangement
301 outer vessel
302 inner vessel

303 opening
304 cap
305 secretion
L longitudinal axis
$L_S$ longitudinal axis of the AM element
$\alpha$ deflection angle Although the present invention has been described in connection with certain specific embodiments for instructional purposes, the present invention is not limited thereto. Accordingly, various modifications, adaptations, and combinations of various features of the described embodiments can be practiced without departing from the scope of the invention as set forth in the claims.

What is claimed is:

1. An application device for positioning an absorptive matrix (AM) element within a body cavity, the application device comprising:
   a tube having a wall, a distal end and a proximal end;
   the AM element being disposed inside the tube in a stored state before exiting the tube towards the distal end of the tube in a released state;
   a release element that slides inside the tube along a longitudinal axis of the tube, wherein the release element axially pushes the AM element along the longitudinal axis towards the distal end of the tube as the release element slides farther into the tube; and
   a deflector disposed towards the distal end of the tube, wherein the deflector bends a portion of the AM element that passes the deflector away from the longitudinal axis of the tube as a remaining portion of the AM element is pushed axially along the longitudinal axis through the tube such that the AM element exits the tube only towards the distal end of the tube, and wherein the AM element is not fixedly attached to any of the tube, the release element or the deflector.

2. The application device of claim 1, wherein the deflector is a portion of the wall of the tube that protrudes from the distal end and bends inward towards the longitudinal axis of the tube, and wherein the AM element is deflected by the deflector after being pushed out of the distal end of the tube.

3. The application device of claim 1, wherein the deflector is a thickened part of the wall of the tube towards the distal end, and wherein the AM element is pushed out of a release opening in the wall of the tube after being deflected by the deflector.

4. The application device of claim 1, wherein the distal end of the tube is formed by a plurality of tongues.

5. The application device of claim 4, wherein at least one of the plurality of tongues has a bending stiffness away from the longitudinal axis that is greater than that of the other of the plurality of tongues.

6. The application device of claim 1, wherein the release element is a push rod and a piston that are slidably mounted within the tube.

7. The application device of claim 1, wherein the release element includes a push rod that passes through a longitudinal side slot in the tube, and wherein the push rod is slidably movable along the longitudinal side slot.

8. The application device of claim 1, wherein the distal end of the tube is closed until the distal end is opened by the AM element being pushed out of the distal end as the release element is slid farther into the tube.

9. The application device of claim 1, wherein a leash is attached to the proximal end of the AM element, and wherein a portion of the leash remains outside the body cavity when the AM element is within the body cavity in the released state.

10. The application device of claim 9, wherein the leash is extended when the tube is removed from the body cavity.

11. The application device of claim 1, wherein the tube is tapered such that the tube has a diameter that decreases towards the distal end.

12. The application device of claim 1, wherein a screw thread is disposed on an inner surface of the tube, and wherein the screw thread is configured to rotate the AM element about the longitudinal axis as the release element pushes the AM element out of the tube.

13. The application device of claim 1, wherein two plate elements protrude in opposite directions circumferentially outwards from the proximal end of the tube.

14. A collection kit for collecting biological secretions from a body cavity, the collection kit comprising:
   a tube of an application device, wherein the tube has a wall, a distal end and a proximal end;
   an absorptive matrix (AM) element of the application device, wherein the AM element is disposed inside the tube in a stored state and outside the tube in a released state;
   a release element of the application device that slides inside the tube along a longitudinal axis of the tube, wherein the release element axially pushes the AM element along the longitudinal axis towards the distal end of the tube and into the body cavity as the release element slides farther into the tube;
   a deflector disposed towards the distal end of the tube, wherein the deflector bends a portion of the AM element that passes the deflector away from the longitudinal axis of the tube as a remaining portion of the AM element is pushed axially along the longitudinal axis through the tube such that the AM element exits the tube only towards the distal end of the tube; and
   a vessel adapted to store the AM element after the AM element has been removed from the body cavity.

15. The collection kit of claim 14, wherein the vessel includes an inner vessel and an outer vessel, and wherein the inner vessel is adapted to contain the AM element.

16. The collection kit of claim 14, wherein the outer vessel is adapted for containing the biological secretions that flow through a hole in the inner vessel to the outer vessel during centrifugation.

17. A method for collecting nasal secretions, the method comprising:
   introducing a distal end of a tube of an application device into a nasal cavity, wherein the tube has a wall, the distal end, a proximal end and a longitudinal axis, wherein an absorptive matrix (AM) element is disposed inside the tube in a stored state before exiting the tube in a released state, and wherein a deflector is disposed towards the distal end of the tube;
   releasing the AM element into the nasal cavity by sliding a release element into the tube such that the release element axially pushes the AM element along the longitudinal axis towards the distal end, wherein the deflector bends a portion of the AM element that passes the deflector away from the longitudinal axis of the tube as a remaining portion of the AM element is pushed axially along the longitudinal axis through the tube such that the AM element exits the tube only towards the distal end of the tube;
   removing the tube from the nasal cavity without removing the AM element from the nasal cavity; and
   removing the AM element from the nasal cavity.

18. The method of claim 17, wherein the AM element is released into the nasal cavity in a predetermined target position.

19. The method of claim 17, wherein the AM element is removed from the nasal cavity at least fifteen minutes after the AM element is released into the nasal cavity.

20. The method of claim 17, wherein the deflector is an extension of the wall of the tube that protrudes from the distal end and bends inward towards the longitudinal axis of the tube.

21. The method of claim 17, wherein the deflector is a thickened part of the wall of the tube towards the distal end, and wherein the AM element is pushed out of a release opening in the wall of the tube after being deflected by the deflector.

\* \* \* \* \*